United States Patent
Hansen et al.

(10) Patent No.: US 11,471,318 B2
(45) Date of Patent: Oct. 18, 2022

(54) DATA COLLECTION SCHEMES FOR A MEDICAL APPLIANCE AND RELATED METHODS

(71) Applicant: Coloplast A/S, Humlebaek (DK)

(72) Inventors: Jais Ask Hansen, Jaegerspris (DK); Lars Erup Larsen, Maaloev (DK); Niels Hvid, Vedbaek (DK); Lars Molzen, Kongens Lyngby (DK); Finn Speiermann, Virum (DK); Klaus Thoegersen, Charlottenlund (DK)

(73) Assignee: Coloplast A/S, Humlebaek (DK)

( * ) Notice: Subject to any disclaimer, the term of this patent is extended or adjusted under 35 U.S.C. 154(b) by 217 days.

(21) Appl. No.: 16/955,039

(22) PCT Filed: Dec. 20, 2018

(86) PCT No.: PCT/DK2018/050385
§ 371 (c)(1),
(2) Date: Jun. 18, 2020

(87) PCT Pub. No.: WO2019/120429
PCT Pub. Date: Jun. 27, 2019

(65) Prior Publication Data
US 2020/0375784 A1   Dec. 3, 2020

(30) Foreign Application Priority Data
Dec. 22, 2017 (DK) .......................... PA 2017 70985

(51) Int. Cl.
*A61F 5/00* (2006.01)
*A61F 5/44* (2006.01)
(Continued)

(52) U.S. Cl.
CPC ............ *A61F 5/4404* (2013.01); *A61F 5/445* (2013.01); *A61B 5/1116* (2013.01); *A61B 5/1118* (2013.01)

(58) Field of Classification Search
CPC ........ A61F 5/4404; A61F 5/445; A61F 5/443; A61F 5/448; A61B 5/116; A61B 5/118
See application file for complete search history.

(56) References Cited

U.S. PATENT DOCUMENTS 6,171,289 B1 * 1/2001 Millot ..................... A61F 5/443
604/336
2013/0324952 A1 * 12/2013 Krystek .................. A61F 5/445
604/318

(Continued)

FOREIGN PATENT DOCUMENTS

WO 2019094635 A1 5/2019

*Primary Examiner* — Ojiako K Nwugo
(74) *Attorney, Agent, or Firm* — Coloplast Corp., Coloplast A/S; Nick Baumann

(57) ABSTRACT

Embodiments of the present disclosure relate to a monitor device for an ostomy system. The monitor device comprises: a processor; memory; and a first interface connected to the processor and the memory. The first interface comprises a plurality of terminals and a data collector. The plurality of terminals includes a first terminal that forms an electrical connection with a first electrode of an ostomy appliance of the ostomy system and a second terminal that forms an electrical connection with a second electrode of the ostomy appliance. The data collector is coupled to the first and second terminals and comprises a data collection configured to collect data from the plurality of terminals according to a primary data collection scheme and collect data from the plurality of terminals according to a secondary data collection scheme. The primary data collection scheme is different from the secondary data collection scheme.

14 Claims, 16 Drawing Sheets

(51) Int. Cl.
  *A61F 5/445*    (2006.01)
  *A61B 5/11*    (2006.01)

(56) References Cited

U.S. PATENT DOCUMENTS

2017/0140103 A1* 5/2017 Angelides ............. A61F 5/4404
2017/0340474 A1* 11/2017 Thirstrup ................ A61F 5/445

* cited by examiner

DATA COLLECTION SCHEMES FOR A MEDICAL APPLIANCE AND RELATED METHODS

The present disclosure relates to an ostomy system, devices thereof and method for manufacturing an ostomy appliance. The ostomy appliance system comprises an ostomy appliance and an ostomy monitor device. In particular, the present disclosure relates to data collection schemes for an ostomy appliance.

BRIEF DESCRIPTION OF THE DRAWINGS

The accompanying drawings are included to provide a further understanding of embodiments and are incorporated into and a part of this specification. The drawings illustrate embodiments and together with the description explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
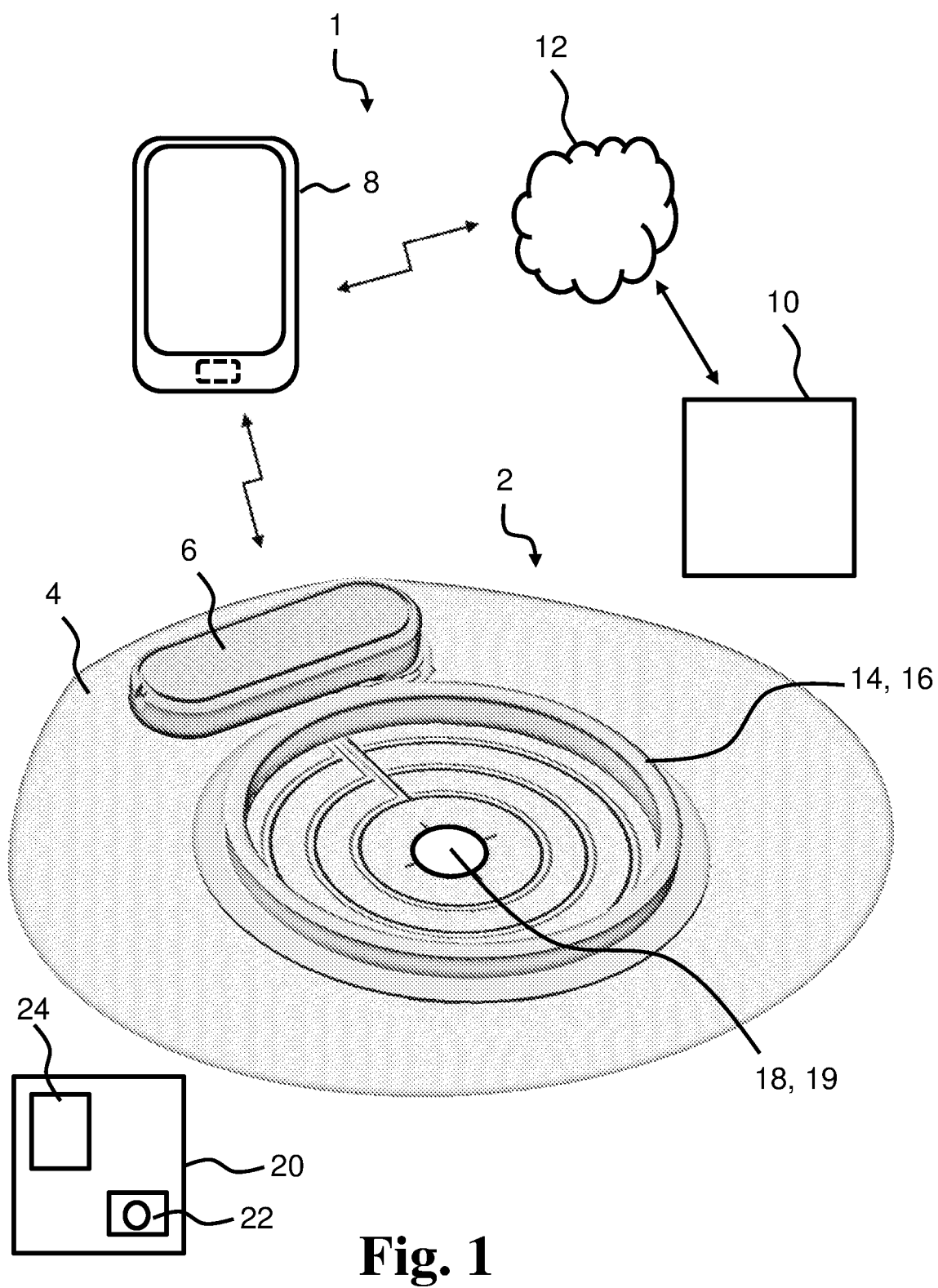
FIG. 1 illustrates an exemplary ostomy system.

Various exemplary embodiments and details are described hereinafter, with reference to the figures when relevant. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

Throughout this disclosure, the words "stoma" and "ostomy" are used to denote a surgically created opening bypassing the intestines or urinary tract system of a person. The words are used interchangeably, and no differentiated meaning is intended. The same applies for any words or phrases derived from these, e.g. "stomal", "ostomies" etc. Also, the solid and liquid wastes emanating from the stoma may be referred to as both stomal "output," "waste(s)," and "fluids" interchangeably. A subject having undergone ostomy surgery may be referred to as "ostomist" or "ostomate"—moreover, also as "patient" or "user". However, in some cases "user" may also relate or refer to a health care professional (HCP), such as a surgeon or an ostomy care nurse or others. In those cases, it will either be explicitly stated, or be implicit from the context that the "user" is not the "patient" him- or herself.

In the following, whenever referring to proximal side or surface of a layer, an element, a device or part of a device, the referral is to the skin-facing side or surface when a user wears the ostomy appliance. Likewise, whenever referring to the distal side or surface of a layer, an element, a device or part of a device, the referral is to the side or surface facing away from the skin when a user wears the ostomy appliance. In other words, the proximal side or surface is the side or surface closest to the user when the appliance is fitted on a user and the distal side is the opposite side or surface—the side or surface furthest away from the user in use.

The axial direction is defined as the direction of the stoma when a user wears the appliance. Thus, the axial direction is generally perpendicular to the skin or abdominal surface of the user.

The radial direction is defined as perpendicular to the axial direction. In some sentences, the words "inner" and "outer" may be used. These qualifiers should generally be perceived with respect to the radial direction, such that a reference to an "outer" element means that the element is farther away from a centre portion of the ostomy appliance than an element referenced as "inner". In addition, "innermost" should be interpreted as the portion of a component forming a centre of the component and/or being adjacent to the centre of the component. In analogy, "outermost" should be interpreted as a portion of a component forming an outer edge or outer contour of a component and/or being adjacent to that outer edge or outer contour.

The use of the word "substantially" as a qualifier to certain features or effects in this disclosure is intended to simply mean that any deviations are within tolerances that would normally be expected by the skilled person in the relevant field.

The use of the word "generally" as a qualifier to certain features or effects in this disclosure is intended to simply mean—for a structural feature: that a majority or major portion of such feature exhibits the characteristic in question, and—for a functional feature or an effect: that a majority of outcomes involving the characteristic provide the effect, but that exceptionally outcomes do no provide the effect.

The present disclosure relates to an ostomy system and devices thereof, such as an ostomy appliance, a base plate for an ostomy appliance, a monitor device, and optionally one or more accessory devices. Further, methods related to the ostomy system and devices thereof are disclosed. An accessory device (also referred to as an external device) may be a mobile phone or other handheld device. An accessory device may be a personal electronic device, e.g. a wearable, such as a watch or other wrist-worn electronic device. An accessory device may be a docking station. The docking station may be configured to electrically and/or mechanically couple the monitor device to the docking station. The docking station may be configured for charging the monitor device and/or configured for transferring data between the monitor device and the docking station. The ostomy system may comprise a server device. The server device may be operated and/or controlled by the ostomy appliance manufacturer and/or a service centre.

The present disclosure provides an ostomy system and devices thereof, such as an ostomy appliance, a base plate for an ostomy appliance, a monitor device, and optionally one or more accessory devices which either alone or together facilitate reliable determination of the nature, severity and rapidness of moisture propagation in the adhesive material provided for attaching the base plate to the skin surface of a user. Depending on the nature of the pattern of moisture propagation in the adhesive, the ostomy system and devices thereof enable providing information to the user about the type of failure, and in turn enable providing an indication to the user of the severity and thus the remaining time frame for replacing the ostomy appliance without experiencing severe leakage and/or skin damage.

The ostomy appliance comprises a base plate and an ostomy pouch (also referred to as an ostomy bag). The ostomy appliance may be a colostomy appliance, an ileostomy appliance or a urostomy appliance. The ostomy appliance may be a two-part ostomy appliance, i.e. the base plate and the ostomy pouch may be releasably coupled e.g. with a mechanical and/or an adhesive coupling, e.g. to allow that a plurality of ostomy pouches can be utilized (exchanged) with one base plate. Further, a two-part ostomy appliance may facilitate correct application of the base plate to skin, e.g. to an improved user sight of the stomal region. The ostomy appliance may be a one-part ostomy appliance, i.e. the base plate and the ostomy pouch may be fixedly attached to each other. The base plate is configured for coupling to a user's stoma and/or skin surrounding the stoma, such as a peristomal skin area.

The base plate comprises a first adhesive layer, also denoted center adhesive layer. During use, the first adhesive layer adheres to the user's skin (peristomal area) and/or to additional seals, such as sealing paste, sealing tape and/or sealing ring. Thus, the first adhesive layer may be configured for attachment of the base plate to the skin surface of a user. The first adhesive layer may have a stomal opening with a center point.

The first adhesive layer may be made of a first composition. The first composition may comprise one or more polyisobutenes and/or styrene-isoprene-styrene. The first composition may comprise one or more hydrocoloids.

The first composition may be a pressure sensitive adhesive composition suitable for medical purposes comprising a rubbery elastomeric base and one or more water soluble or water swellable hydrocolloids. The first composition may comprise one or more polybutenes, one or more styrene copolymers, one or more hydrocolloids, or any combination thereof. The combination of the adhesive properties of the polybutenes and the absorbing properties of the hydrocolloids renders the first composition suitable for use in ostomy appliances. The styrene copolymer may for example be a styrene-butadiene-styrene block copolymer or a styrene-isoprene-styrene block copolymer. Preferably, one or more styrene-isoprene-styrene (SIS) block type copolymers are employed. The amount of styrene block-copolymer may be from 5% to 20% of the total adhesive composition. The butene component is suitably a conjugated butadiene polymer selected from polybutadiene, polyisoprene. The polybutenes are preferably present in an amount of from 35-50% of the total adhesive composition. Preferably, the polybutene is polyisobutylene (PIB). Suitable hydrocolloids for incorporation in the first composition are selected from naturally occurring hydrocolloids, semisynthetic hydrocolloids and synthetic hydrocolloids. The first composition may comprise 20-60% hydrocolloids. A preferred hydrocolloid is carboxymethyl cellulose (CMC). The first composition may optionally contain other components, such as fillers, tackifiers, plasticizers, and other additives.

The first adhesive layer may have a plurality of sensor point openings. A sensor point opening of the first adhesive layer is optionally configured to overlap a part of an electrode, e.g. to form a sensor point.

The sensor point openings of the first adhesive layer may comprise primary sensor point openings. The primary sensor point openings may comprise one or more primary first sensor point openings and one or more primary second sensor point openings, the primary first sensor point openings configured to overlap parts of an electrode and the primary second sensor point openings configured to overlap parts of another electrode different from the electrode at least partly overlapped by the primary first sensor point openings.

The sensor point openings of the first adhesive layer may comprise secondary sensor point openings. The secondary sensor point openings may comprise one or more secondary first sensor point openings and one or more secondary second sensor point openings, the secondary first sensor point openings configured to overlap parts of an electrode and the secondary second sensor point openings configured to overlap parts of another electrode different from the electrode at least partly overlapped by the secondary first sensor point openings.

The sensor point openings of the first adhesive layer may comprise tertiary sensor point openings. The tertiary sensor point openings may comprise one or more tertiary first sensor point openings and one or more tertiary second sensor point openings, the tertiary first sensor point openings configured to overlap parts of an electrode and the tertiary second sensor point openings configured to overlap parts of another electrode different from the electrode at least partly overlapped by the tertiary first sensor point openings.

The first adhesive layer may have a substantially uniform thickness. The first adhesive layer may have a thickness in the range from 0.1 mm to 1.5 mm, e.g. in the range from 0.2 mm to 1.2 mm, such as 0.8 mm or 1.0 mm.

The first adhesive layer may have a primary thickness in a primary part of the first adhesive layer, e.g. in a primary region within a primary radial distance or in a primary radial distance range from the center point of the stomal opening. The primary thickness may be in the range from 0.2 mm to 1.5 mm. such as about 1.0 mm. The primary radial distance may be in the range from 20 mm to 50 mm, such as in the range from 25 mm to 35 mm, e.g. 30 mm.

The first adhesive layer may have a secondary thickness in a secondary part of the first adhesive layer, e.g. in a secondary region outside a secondary radial distance or in a secondary radial distance range from the center point of the stomal opening. The secondary thickness may be in the range from 0.2 mm to 1.0 mm, such as about 0.5 mm. The secondary radial distance may be in the range from 20 mm to 50 mm, such as in the range from 25 mm to 35 mm, e.g. 30 mm.

The base plate may comprise a second layer. The second layer may be an adhesive layer, also denoted rim adhesive layer. The second layer may have a second radial extension that is larger than a first radial extension of the first adhesive layer at least in a first angular range of the base plate. Accordingly, a part of a proximal surface of the second layer may be configured for attachment to the skin surface of a user. The part of a proximal surface of the second layer configured for attachment to the skin surface of a user is also denoted the skin attachment surface of the second adhesive layer. The second layer may have a stomal opening with a center point.

The second adhesive layer may be made of a second composition. The second composition may comprise one or more polyisobutenes and/or styrene-isoprene-styrene. The second composition may comprise one or more hydrocoloids.

The second composition may be a pressure sensitive adhesive composition suitable for medical purposes comprising a rubbery elastomeric base and one or more water soluble or water swellable hydrocolloids. The second composition may comprise one or more polybutenes, one or more styrene copolymers, one or more hydrocolloids, or any combination thereof. The combination of the adhesive properties of the polybutenes and the absorbing properties of the hydrocolloids renders the second composition suitable for use in ostomy appliances. The styrene copolymer may for example be a styrene-butadiene-styrene block copolymer or a styrene-isoprene-styrene block copolymer. Preferably, one or more styrene-isoprene-styrene (SIS) block type copolymers are employed. The amount of styrene block-copolymer may be from 5% to 20% of the total adhesive composition. The butene component is suitably a conjugated butadiene polymer selected from polybutadiene, polyisoprene. The polybutenes are preferably present in an amount of from 35-50% of the total adhesive composition. Preferably, the polybutene is polyisobutylene (PIB). Suitable hydrocolloids for incorporation in the second composition are selected from naturally occurring hydrocolloids, semisynthetic hydrocolloids and synthetic hydrocolloids. The second composition may comprise 20-60% hydrocolloids. A preferred hydrocolloid is carboxymethyl cellulose (CMC). The second composition may optionally contain other components, such as fillers, tackifiers, plasticizers, and other additives.

Different ratio of contents may change properties of the first and/or second adhesive layers. The second adhesive layer and the first adhesive layer may have different properties. The second adhesive layer (second composition) and the first adhesive layer (first composition) may have different ratios of polyisobutenes, styrene-isoprene-styrene, and/or hydrocoloids. For example, the second adhesive layer may provide a stronger attachment to the skin compared to attachment to the skin provided by the first adhesive layer. Alternatively or additionally, the second adhesive layer may be thinner than the first adhesive layer. Alternatively or additionally, the second adhesive layer may be less water and/or sweat absorbing than the first adhesive layer. Alternatively or additionally, the second adhesive layer may be less mouldable than the first adhesive layer. The second adhesive layer may provide a second barrier against leakage.

The second layer may have a substantially uniform thickness. The second layer may have a thickness in the range from 0.1 mm to 1.5 mm, e.g. in the range from 0.2 mm to 1.0 mm, such as 0.5 mm, 0.6 mm, or 0.7 mm.

The base plate comprises one or more electrodes, such as a plurality of electrodes, such as two, three, four, five, six, seven or more electrodes. The electrodes, e.g. some or all the electrodes, may be arranged between the first adhesive layer and the second adhesive layer. The electrodes may be arranged in an electrode assembly, e.g. an electrode layer. An electrode comprises a connection part for connecting the electrodes to other components and/or interface terminals. An electrode may comprise one or more conductor parts and/or one or more sensing parts. The electrode assembly may be arranged between the first adhesive layer and the second adhesive layer. The base plate, e.g. the electrode assembly, may comprise a first electrode, a second electrode and optionally a third electrode. The base plate, e.g. the electrode assembly, may comprise a fourth electrode and/or a fifth electrode. The base plate, e.g. the electrode assembly, optionally comprises a sixth electrode. The base plate, e.g. the electrode assembly, may comprise a ground electrode. The ground electrode may comprise a first electrode part. The first electrode part of the ground electrode may form a ground for the first electrode. The ground electrode may comprise a second electrode part. The second electrode part of the ground electrode may form a ground for the second electrode. The ground electrode may comprise a third electrode part. The third electrode part of the ground electrode may form a ground for the third electrode. The ground electrode may comprise a fourth electrode part. The fourth electrode part of the ground electrode may form a ground for the fourth electrode and/or the fifth electrode.

The ground electrode or electrode parts of the ground electrode may be configured as or form a (common) reference electrode for some or all of the other electrodes of the electrode assembly. The ground electrode may also be denoted reference electrode.

The electrodes are electrically conductive and may comprise one or more of metallic (e.g. silver, copper, gold, titanium, aluminium, stainless steel), ceramic (e.g. ITO), polymeric (e.g. PEDOT, PANI, PPy), and carbonaceous (e.g. carbon black, carbon nanotube, carbon fibre, graphene, graphite) materials.

The ground electrode may comprise a first electrode part and a second electrode part, the first electrode part forming the ground for the first electrode and the second electrode part forming the ground for the second electrode. The first electrode part may form a closed loop.

The electrodes are electrically conductive and may comprise one or more of metallic (e.g. silver, copper, gold, titanium, aluminium, stainless steel), ceramic (e.g. ITO), polymeric (e.g. PEDOT, PANI, PPy), and carbonaceous (e.g. carbon black, carbon nanotube, carbon fibre, graphene, graphite) materials.

Two electrodes of the electrode assembly may form a sensor. The first electrode and the ground electrode (e.g. first electrode part of the ground electrode) may form a first sensor or first electrode pair. The second electrode and the ground electrode (e.g. second electrode part of the ground electrode) may form a second sensor or second electrode pair. The third electrode and the ground electrode (e.g. third electrode part of the ground electrode) may form a third sensor or third electrode pair. The fourth electrode and the ground electrode (e.g. fourth electrode part of the ground electrode) may form a fourth sensor or fourth electrode pair. The fifth electrode and the ground electrode (e.g. fifth electrode part of the ground electrode) may form a fifth sensor or fifth electrode pair. The fourth electrode and the fifth electrode may form a sixth sensor or sixth electrode pair.

An electrode may comprise a sensing part or a plurality of sensing parts, i.e. the part(s) of an electrode that are used for sensing. The first electrode may comprise a first sensing part. The first sensing part may contact the first adhesive layer and is optionally arranged at least partly annularly around the stomal opening. The first electrode may comprise a first conductor part insulated from the first adhesive layer, e.g. by a masking element arranged between the first conductor part and the first adhesive layer. The first sensing part may extend at least 270 degrees around the stomal opening, such as at least 300 degrees around the stomal opening. The first sensing part of the first electrode may be arranged at a first ground distance from the first electrode part of the ground electrode. The first ground distance may be less than 5 mm, such as less than 3 mm, e.g. about 1.0 mm.

The second electrode may comprise a second sensing part. The second sensing part may contact the first adhesive layer. The second sensing part may be arranged at least partly annularly around the stomal opening. The second sensing part may extend at least 270 degrees around the stomal opening, such as at least 300 degrees around the stomal opening. The second sensing part of the second electrode may be arranged at a second ground distance from the second electrode part of the ground electrode. The second ground distance may be less than 5 mm, such as less than 3 mm, e.g. about 1.0 mm.

The first sensing part may be arranged at a first radial distance from the center point and the second sensing part may be arranged at a second radial distance from the center point. The second radial distance may be larger than the first radial distance. The second electrode may comprise a second conductor part insulated from the first adhesive layer, e.g. by a masking element arranged between the second conductor part and the first adhesive layer. The first radial distance may vary as a function of an angular position with respect to a zero direction from the center point. The second radial distance may vary as a function of an angular position with respect to a zero direction from the center point. The zero direction may be defined as the vertical upward direction when the base plate is in its intended wearing position on an upstanding user.

The first radial distance may be in the range from 5 mm to 40 mm, such as in the range from 10 mm to 25 mm, e.g. about 14 mm. The second radial distance may be in the range from 10 mm to 50 mm, such as in the range from 10 mm to 25 mm, e.g. about 18 mm.

The base plate may comprise a third electrode comprising a third connection part. The ground electrode may form a ground for the third electrode. The ground electrode may comprise a third electrode part, the third electrode part forming the ground for the third electrode. The third electrode may comprise a third conductor part insulated from the first adhesive layer, e.g. by a masking element arranged between the third conductor part and the first adhesive layer. The third electrode may comprise a third sensing part, the third sensing part contacting the first adhesive layer. The third sensing part may be arranged at least partly annularly around the stomal opening. The third sensing part may be arranged at a third radial distance from the center point. The third radial distance may be larger than the first radial distance and/or larger than the second radial distance. The third radial distance may be in the range from 15 mm to 50 mm. such as in the range from 20 mm to 30 mm, e.g. about 26 mm. The third sensing part may extend at least 270 degrees around the stomal opening, such as at least 300 degrees around the stomal opening. The third sensing part of the third electrode may be arranged at a third ground distance from the third electrode part of the ground electrode. The third ground distance may be less than 5 mm, such as less than 3 mm, e.g. about 1.0 mm. A base plate with a ground electrode, a first electrode, a second electrode, and a third electrode allow for a failsafe base plate in case e.g. the first electrode is cut or otherwise destroyed during preparation of the base plate.

The base plate may comprise a fourth electrode comprising a fourth connection part. The ground electrode may form a ground for the fourth electrode. The ground electrode may comprise a fourth electrode part, the fourth electrode part forming the ground for the fourth electrode. The fourth electrode may comprise one or a plurality of fourth sensing parts, such as at least five fourth sensing parts. The fourth sensing parts may be distributed around the stomal opening or a center point thereof. The fourth sensing parts may be arranged at respective fourth radial distances from the center point. The fourth radial distance(s) may be larger than the third radial distance. The fourth radial distance(s) may be in the range from 25 mm to 50 mm, such as about 30 mm.

The base plate may comprise a fifth electrode comprising a fifth connection part. The ground electrode may form a ground for the fifth electrode. The ground electrode may comprise a fifth electrode part, the fifth electrode part forming the ground for the fifth electrode. The fifth electrode may comprise one or a plurality of fifth sensing parts, such as at least five fifth sensing parts. The fifth sensing parts may be distributed around the stomal opening or a center point thereof. The fifth sensing parts may be arranged at respective fifth radial distances from the center point. The fifth radial distance may be larger than the third radial distance. The fifth radial distance may be equal to or larger than the fourth radial distance. The fifth radial distance(s) may be in the range from 25 mm to 50 mm, such as about 30 mm.

The first electrode may form an open loop. The second electrode may form an open loop, and/or the third electrode may form an open loop. The fourth electrode may form an open loop. The fifth electrode may form an open loop. Open loop electrode(s) enables electrode arrangement in few or a single electrode layer.

The base plate may comprise a second adhesive layer, wherein the plurality of electrodes is arranged between the first adhesive layer and the second adhesive layer.

The electrode assembly may comprise a support layer, also denoted a support film. One or more electrodes may be formed, e.g. printed, on the proximal side of the support layer. One or more electrodes may be formed, e.g. printed, on the distal side of the support layer. The electrode assembly may have a stomal opening with a center point.

The support layer may comprise polymeric (e.g. polyurethane, PTFE, PVDF) and/or ceramic (e.g. alumina, silica) materials. In one or more exemplary base plates, the support layer is made of thermoplastic polyurethane (TPU). The support layer material may be made of or comprise one or more of polyester, a thermoplastic elastomer (TPE), polyamide, polyimide, Ethylene-vinyl acetate (EVA), polyurea, and silicones.

Exemplary thermoplastic elastomers of the support layer are styrenic block copolymers (TPS, TPE-s), thermoplastic polyolefin elastomers (TPO, TPE-o), thermoplastic Vulcanizates (TPV, TPE-v), thermoplastic polyurethanes (TPU), thermoplastic copolyester (TPC, TPE-E), and thermoplastic polyamides (TPA, TPE-A).

The electrode assembly/base plate may comprise a masking element configured to insulate at least parts of the electrodes from the first adhesive layer of the base plate. The masking element may comprise one or more, such as a plurality of, sensor point openings. The sensor point openings may comprise primary sensor point openings and/or secondary sensor point openings. The sensor point openings may comprise tertiary sensor point opening(s). The sensor point openings may comprise quaternary sensor point opening(s) A sensor point opening of the masking element overlaps at least one electrode of the electrode assembly when seen in the axial direction, e.g. to form a sensor point. For example, a primary sensor point opening may overlap a part of the ground electrode and/or a part of the fourth electrode. A secondary sensor point opening may overlap a part of the fourth electrode and/or a part of the fifth electrode. A tertiary sensor point opening may overlap a part of the fifth electrode and/or a part of the ground electrode.

The masking element may comprise one or more, such as a plurality of, terminal openings. A terminal opening may overlap with one or more connection parts of electrodes. In one or more exemplary base plates, each terminal opening overlaps with a single connection part of an electrode. The masking element may comprise polymeric (e.g. polyurethane, PTFE, PVDF) and/or ceramic (e.g. alumina, silica) materials. In one or more exemplary base plates, the masking element is made of or comprises thermoplastic polyurethane (TPU). In one or more exemplary base plates, the masking element is made of or comprises polyester. The masking element material may be made of or comprise one or more of polyester, a thermoplastic elastomer (TPE), polyamide, polyimide, Ethylene-vinyl acetate (EVA), polyurea, and silicones.

Exemplary thermoplastic elastomers of the masking element are styrenic block copolymers (TPS, TPE-s), thermoplastic polyolefin elastomers (TPO, TPE-o), thermoplastic Vulcanizates (TPV, TPE-v), thermoplastic polyurethanes (TPU), thermoplastic copolyester (TPC, TPE-E), and thermoplastic polyamides (TPA, TPE-A).

The base plate may comprise a first intermediate element. The first intermediate element may be arranged between the electrodes/electrode layer and the first adhesive layer and/or between the second layer and the first adhesive layer. The first intermediate layer may be made of an insulating material.

The base plate may comprise a release liner. The release liner is a protective layer that protects adhesive layer(s) during transport and storage and is peeled off by the user prior to applying the base plate on the skin. The release liner may have a stomal opening with a center point.

The base plate may comprise a top layer. The top layer is a protective layer protecting the adhesive layer(s) from external strains and stress when the user wears the ostomy appliance. The electrodes, e.g. some or all the electrodes, may be arranged between the first adhesive layer and the top layer. The top layer may have a stomal opening with a center point. The top layer may have a thickness in the range from 0.01 mm to 1.0 mm, e.g. in the range from 0.02 mm to 0.2 mm, such as 0.04 mm. The top layer may have a stomal opening with a center point.

The base plate comprises a monitor interface. The monitor interface may be configured for electrically and/or mechanically connecting the ostomy appliance (base plate) to the monitor device. The monitor interface may be configured for wirelessly connecting the ostomy appliance (base plate) to the monitor device. Thus, the monitor interface of the base plate is configured to electrically and/or mechanically couple the ostomy appliance and the monitor device.

The monitor interface of the base plate may comprise, e.g. as part of a first connector of the monitor interface, a coupling part for forming a mechanical connection, such as a releasable coupling between the monitor device and the base plate. The coupling part may be configured to engage with a coupling part of the monitor device for releasably coupling the monitor device to the base plate.

The monitor interface of the base plate may comprise, e.g. as part of a first connector of the monitor interface, a plurality of terminals, such as two, three, four, five, six, seven or more terminals, for forming electrical connections with respective terminals of the monitor device. The monitor interface may comprise a ground terminal element forming a ground terminal. The monitor interface may comprise a first terminal element forming a first terminal, a second terminal element forming a second terminal and optionally a third terminal element forming a third terminal. The monitor interface may comprise a fourth terminal element forming a fourth terminal and/or a fifth terminal element forming a fifth terminal. The monitor interface optionally comprises a sixth terminal element forming a sixth terminal. The terminal elements of the monitor interface may contact respective electrodes of the base plate/electrode assembly. The first intermediate element may be arranged between the terminal elements and the first adhesive layer. The first intermediate element may cover or overlap terminal element(s) of the base plate when seen in the axial direction. Thus, the first adhesive layer may be protected or experience more evenly distributed mechanical stress from the terminal elements of the base plate, in turn reducing the risk of terminal elements penetrating or otherwise damaging the first adhesive layer. The first intermediate element may protect or mechanically and/or electrically shield the first adhesive layer from the terminal elements of the base plate.

A terminal element, such as the ground terminal element, the first terminal element, the second terminal element, the third terminal element, the fourth terminal element, the fifth terminal element and/or the sixth terminal element, may comprise a distal end and a proximal end. A terminal element, such as the ground terminal element, the first terminal element, the second terminal element, the third terminal element, the fourth terminal element, the fifth terminal element and/or the sixth terminal element, may comprise a distal part, a centre part, and/or a proximal part. The distal part may be between the distal end and the centre part. The proximal part may be between the proximal end and the centre part. The proximal end/proximal part of a terminal element may contact a connection part of an electrode. A terminal element, such as the ground terminal element, the first terminal element, the second terminal element, the third terminal element, the fourth terminal element, the fifth terminal element and/or the sixth terminal element, may be gold plated copper.

The base plate may comprise a coupling ring or other coupling member for coupling an ostomy pouch to the base plate (two-part ostomy appliance). The center point may be defined as a center of the coupling ring.

The base plate has a stomal opening with a center point. The size and/or shape of the stomal opening is typically adjusted by the user or nurse before application of the ostomy appliance to accommodate the user's stoma. In one or more exemplary base plates, the user forms the stomal opening during preparation of the base plate for application.

A monitor device for an ostomy system comprising an ostomy appliance with a base plate is disclosed, the monitor device comprising a processor configured to apply a processing scheme; memory; a first interface connected to the processor and the memory, the first interface configured for collecting ostomy data from the base plate coupled to the first interface, the ostomy data comprising one or more, such as all, of first ostomy data from a first electrode pair of the base plate, second ostomy data from a second electrode pair of the base plate, and optionally third ostomy data from a third electrode pair of the base plate; and a second interface connected to the processor. To apply a processing scheme comprises obtain first parameter data based on the first ostomy data; obtain second parameter data based on the second ostomy data; and optionally obtain third parameter data based on the third ostomy data. To apply a processing scheme comprises determine an operating state of the base plate of the ostomy appliance. To determine the operating state of the base plate may be based on one or more, such as all, of the first parameter data, the second parameter data, the third parameter data, and fourth parameter data. The operating state may be indicative of a degree of radial erosion and/or radial swelling of the base plate, such as of the first adhesive layer, and/or an acute leakage risk for the ostomy appliance. The monitor device may be configured to transmit a monitor signal comprising monitor data indicative of the determined operating state of the base plate via the second interface. The monitor device may be configured to, in accordance with a determination that the operating state is a first operating state, transmit a first monitor signal comprising monitor data indicative of the first operating state of the base plate via the second interface. The monitor device may be configured to, in accordance with a determination that the operating state is a second operating state, transmit a second monitor signal comprising monitor data indicative of the second operating state of the base plate via the second interface.

An operating state in the present disclosure is indicative of the dynamic internal state of the ostomy appliance (e.g. of the base plate of the ostomy appliance currently being worn by the user) optionally related to adhesive performance of the ostomy appliance. Adhesive performance of the ostomy appliance may be related to an internal condition of the ostomy appliance (e.g. of the base plate of the ostomy appliance), such as an internal condition of an adhesive layer of the ostomy appliance. The adhesive performance, and thereby the operating state may be affected by several factors, such as humidity, temperature, misplacement of the ostomy appliance on the stoma, and/or malfunction of the ostomy appliance. The one or more factors alone or in combination impact the adhesive performance of the ostomy appliance. The operating state may be varying in time. The operating state may be indicative of a degree of erosion of the base plate.

Adhesive performance may be indicative of wear property, e.g. wear time and/or wear comfort. The operating state may comprise at least one of: a wear time, a quality of adhesion, and a moisture pattern representation. Wear time may comprise average wear time, nominal wear time, minimal wear time, maximal wear time, median wear time, and/or any of other statistical metric derivable from wear time. Wear time may comprise remaining wear time and/or current wear time and/or elapsed wear time. A quality of adhesion may comprise a metric indicative of erosion of a layer of the base plate, such as of the first adhesive layer. A moisture pattern representation may comprise one or more metrics or parameters representative or indicative of a moisture pattern (e.g. a moisture pattern type), e.g. a moisture pattern of the first adhesive layer.

An operating state may be configured to indicate whether the ostomy appliance is properly operational based on its adhesive performance (e.g. wear property, e.g. wear time and/or wear comfort). For example, the operating state may be indicative of the severity and/or imminence of a leakage (e.g. low, medium, high or acute).

In one or more exemplary monitor devices, the processor is configured to apply a processing scheme, the first interface is connected to the processor and the memory, and the first interface is configured for collecting ostomy data from the base plate coupled to the first interface. The ostomy data may comprise one or more, such as all, of first ostomy data from a first electrode pair of the base plate, second ostomy data from a second electrode pair of the base plate, and third ostomy data from a third electrode pair of the base plate. A second interface is connected to the processor. To apply a processing scheme may comprise one or more of obtain first parameter data based on the first ostomy data; obtain second parameter data based on the second ostomy data; and obtain third parameter data based on the third ostomy data. To apply a processing scheme may comprise determine an operating state of the base plate of the ostomy appliance based on one or more, such as all, of the first parameter data, the second parameter data and the third parameter data. The operating state may be indicative of a degree of radial erosion of the base plate, such as of the first adhesive layer, and/or an acute leakage risk for the ostomy appliance. The monitor device is configured to, in accordance with a determination that the operating state is a first operating state, transmit a first monitor signal comprising monitor data indicative of the first operating state of the base plate via the second interface; and/or in accordance with a determination that the operating state is a second operating state, transmit a second monitor signal comprising monitor data indicative of the second operating state of the base plate via the second interface.

In one or more exemplary monitor devices, the first operating state of the base plate corresponds to a situation wherein the first adhesive layer of the base plate has experienced a first degree of radial erosion, e.g. the first adhesive layer is eroded to a first radial distance of the first electrode pair but not to a second radial distance of the second electrode pair.

In one or more exemplary monitor devices, the second operating state of the base plate corresponds to a situation wherein the first adhesive layer of the base plate has experienced a second degree of radial erosion, e.g. the first adhesive layer is eroded to the second radial distance of the second electrode pair but not to a third radial distance of the third electrode pair.

To obtain first parameter data based on the first ostomy data may comprise determining one or more first parameters based on the first ostomy data. To obtain second parameter data based on the second ostomy data may comprise determining one or more second parameters based on the second ostomy data. To obtain third parameter data based on the third ostomy data may comprise determining one or more third parameters based on the third ostomy data. In one or more exemplary monitor devices, determination of an operating state may be based on one or more first parameters, such as first primary parameter and/or first secondary parameter of first parameter data. In one or more exemplary monitor devices, determination of an operating state may be based on one or more second parameters, such as second primary parameter and/or second secondary parameter of the second parameter data. In one or more exemplary monitor devices, determination of an operating state may be based on one or more third parameters, such as third primary parameter and/or third secondary parameter of the third parameter data. In one or more exemplary monitor devices, determination of an operating state may be based on one or more fourth parameters, such as fourth primary parameter and/or fourth secondary parameter of the fourth parameter data.

The monitor device comprises a monitor device housing optionally made of a plastic material. The monitor device housing may be an elongate housing having a first end and a second end. The monitor device housing may have a length or maximum extension along a longitudinal axis in the range from 1 cm to 15 cm. The monitor device housing may have a width or maximum extension perpendicular to the longitudinal axis in the range from 0.5 cm to 3 cm. The monitor device housing may be curve-shaped.

The monitor device comprises a first interface connected to the processor. The first interface may be configured as an appliance interface for electrically and/or mechanically connecting the monitor device to the ostomy appliance. Thus, the appliance interface is configured to electrically and/or mechanically couple the monitor device and the ostomy appliance. The first interface may be configured as an accessory device interface for electrically and//or mechanically connecting the monitor device to an accessory device, such as a docking station. The first interface may be configured for coupling to a docking station of the ostomy system, e.g. for charging the monitor device and/or for data transfer between the monitor device and the docking station.

The first interface of the monitor device may comprise a plurality of terminals, such as two, three, four, five, six, seven or more terminals, for forming electrical connections with respective terminals and/or electrodes of the ostomy appliance. One or more terminals of the first interface may be configured for forming electrical connections with an accessory device, e.g. with respective terminals of a docking station. The first interface may comprise a ground terminal. The first interface may comprise a first terminal, a second terminal and optionally a third terminal. The first interface may comprise a fourth terminal and/or a fifth terminal. The first interface optionally comprises a sixth terminal. In one or more exemplary monitor devices, the first interface has M terminals, wherein M is an integer in the range from 4 to 8.

The first interface of the monitor device may comprise a coupling part for forming a mechanical connection, such as a releasable coupling between the monitor device and the base plate. The coupling part and the terminals of the first interface form (at least part of) a first connector of the monitor device.

The monitor device comprises a power unit for powering the monitor device. The power unit may comprise a battery. The power unit may comprise charging circuitry connected to the battery and terminals of the first interface for charging the battery via the first interface, e.g. the first connector. The first interface may comprise separate charging terminal(s) for charging the battery.

The monitor device may comprise a sensor unit with one or more sensors. The sensor unit is connected to the processor for feeding sensor data to the processor. The sensor unit may comprise an accelerometer for sensing acceleration and provision of acceleration data to the processor. The sensor unit may comprise a temperature sensor for provision of temperature data to the processor.

The monitor device comprises a second interface connected to the processor. The second interface may be configured as an accessory interface for connecting, e.g. wirelessly connecting, the monitor device to one or more accessory devices. The second interface may comprise an antenna and a wireless transceiver, e.g. configured for wireless communication at frequencies in the range from 2.4 to 2.5 GHz. The wireless transceiver may be a Bluetooth transceiver, i.e. the wireless transceiver may be configured for wireless communication according to Bluetooth protocol, e.g. Bluetooth Low Energy, Bluetooth 4.0, Bluetooth 5. The second interface optionally comprises a loudspeaker and/or a haptic feedback element for provision of an audio signal and/or haptic feedback to the user, respectively. The processor may be configured to transmit a monitor signal, such as third monitor signal and/or fourth monitor signal via the loudspeaker. The processor may be configured to transmit a monitor signal, such as one or more, e.g. all, of first monitor signal, second monitor signal, third monitor signal, fourth monitor signal and default monitor signal, as a wireless monitor signal via the antenna and the wireless transceiver.

In one or more exemplary ostomy systems, the monitor device forms an integrated part of the ostomy appliance, e.g. the monitor device may form an integrated part of a base plate of the ostomy appliance.

The first parameter data, the second parameter data, and the third parameter data may be indicative of resistance between the first electrode pair, the second electrode pair, and the third electrode pair, respectively. The first parameter data, the second parameter data, and the third parameter data may be indicative of voltage between the first electrode pair, the second electrode pair, and the third electrode pair, respectively (and thus indicative of resistance). The first parameter data, the second parameter data, and the third parameter data may be indicative of current between the first electrode pair, the second electrode pair, and the third electrode pair, respectively (and thus indicative of resistance).

The first parameter data, the second parameter data, and the third parameter data may be indicative of resistance between the first electrode pair, the second electrode pair, and the third electrode pair, respectively.

The first parameter data, the second parameter data, and the third parameter data may be indicative of a rate of change in resistance between the first electrode pair, the second electrode pair, and the third electrode pair, respectively. In one or more exemplary monitor devices, the first parameter data, the second parameter data, and the third parameter data may be indicative of a rate of change in voltage between the first electrode pair, the second electrode pair, and the third electrode pair, respectively. In one or more exemplary monitor devices, the first parameter data, the second parameter data, and the third parameter data may be indicative of a rate of change in current between the first electrode pair, the second electrode pair, and the third electrode pair, respectively.

To determine an operating state of the base plate of the ostomy appliance may comprise to determine an operating state from a set of operating states. In other words, to determine an operating state may comprise selecting an operating state from a set of predefined operating states. The set of predefined operating states may comprise a number of operating states, such as at least two operating states, at least three operating states, at least four operating states, at least five operating states. The number of operating states may be in the range from four to twenty. In one or more exemplary monitor devices, the number of operating states in the set of predefined operating states. is larger than ten, such as larger than 20 or even larger than 50.

In one or more exemplary monitor devices, the processor is configured to determine an operating state of the base plate if a change criterion is fulfilled. The change criterion may be based on the first parameter data, the second parameter data and/or the third parameter data. The change criterion may be fulfilled if parameter data changes, e.g. if a change in parameter data is larger than a change threshold. Thus, operating state determination may be conditional or dependent on a change in the parameter data, in turn leading to an optimum use of power or battery resources in the monitor device since operating state determination is only performed when there may be a change in the operating state because of the change in parameter data.

In one or more exemplary monitor devices, to determine an operating state of the base plate is based on a first criterion set based on the first parameter data and/or the second parameter data, wherein the operating state is determined to be the first operating state if the first criteria set is satisfied. The first criteria set may comprise one or more first criteria based on one or more of first parameter data, second parameter data and third parameter data. The first criteria set may comprise a first primary criterion based on the first parameter data. The first criteria set may comprise a first secondary criterion based on the second parameter data. The first criteria set may comprise a first tertiary criterion based on the third parameter data.

In one or more exemplary monitor devices, to determine an operating state of the base plate may be based on a first threshold set comprising one or a plurality of first threshold values. The first threshold set may comprise one or a plurality of threshold values, e.g. to be applied in the first criteria set. The first threshold set may comprise a first primary threshold value. The first threshold set may comprise a first secondary threshold value. The first threshold set may comprise a first tertiary threshold value.

The first criteria set may be given by or at least may comprise:

($P\_1\_1 < TH\_1\_1$),
($P\_2\_1 > TH\_1\_2$), and
($P\_3\_1 > TH\_1\_3$), wherein $P\_1\_1$ is a first primary parameter based on the first parameter data, $TH\_1\_1$ is a first primary threshold value, $P\_2\_1$ is a second primary parameter based on the second parameter data, $TH\_1\_2$ is a first secondary threshold value, $P\_3\_1$ is a third primary parameter based on the third parameter data, and $TH\_1\_3$ is a first tertiary threshold value, and wherein the first operating state is indicative of low degree of radial erosion on the base plate. The first threshold values ($TH\_1\_1$, $TH\_1\_2$ and $TH\_1\_3$) may be the same or different, e.g. depending on the electrode configuration of the base plate. The first tertiary criterion ($P\_3\_1 < TH\_1\_3$) may be omitted in the first criteria set. The first operating state, e.g. indicative of low degree of radial erosion on the base plate may be indicative of a radial progression of moisture to the first electrode pair (but not to the second electrode pair and not to the third electrode pair) which corresponds to e.g. an un-alarming and/or normal radial progression of moisture.

In one or more exemplary embodiments, when the first parameter data, the second parameter data and the third parameter data are each respectively indicative of resistance between the first electrode pair, the second electrode pair and the third electrode pair respectively, the first threshold values ($TH\_1\_1$, $TH\_1\_2$ and $TH\_1\_3$) may correspond to first resistance threshold values. In one or more exemplary embodiments, the first primary threshold value $TH\_1\_1$ may correspond to an upper resistance threshold value. An upper resistance threshold value may be set to a value which is less than 30 Mega-Ohms, such as 25 Mega-Ohms, such as 20.5 Mega-Ohms, such as 20.4 Mega-Ohms. In one or more exemplary embodiments, the first secondary threshold value $TH\_1\_2$ may correspond to the upper resistance threshold value. In one or more exemplary embodiments, the first tertiary threshold value $TH\_1\_3$ may correspond to the upper resistance threshold value.

The first primary parameter $P\_1\_1$ may be indicative of the resistance between the first electrode pair (first electrode and first electrode part of the ground electrode) of the base plate. The first parameter data may comprise a first secondary parameter which may be derived from the first primary parameter, and/or a first tertiary parameter, which may be derived from the first primary parameter. A first secondary parameter $P\_1\_2$ may comprise or be a gradient derived from the first primary parameter. In one or more embodiments, a first primary parameter $P\_1\_1$ may be indicative of a voltage between the first electrode pair (first electrode and first electrode part of the ground electrode) of the base plate.

In one or more exemplary embodiments, when the first parameter data, the second parameter data and the third parameter data are each respectively indicative of voltage between the first electrode pair, the second electrode pair and the third electrode pair respectively, the first threshold values ($TH\_1\_1$, $TH\_1\_2$ and $TH\_1\_3$) may correspond to first voltage threshold values. In one or more exemplary embodiments, the first primary threshold value $TH\_1\_1$ may correspond to an upper voltage threshold value. An upper voltage threshold value may be set to a value less than 5 Volts, such as 3 Volts, such as 2, 86 Volts. In one or more exemplary embodiments, the first secondary threshold value $TH\_1\_2$ may correspond to the upper voltage threshold value. In one or more exemplary embodiments, the first tertiary threshold value $TH\_1\_3$ may correspond to the upper voltage threshold value.

The first criteria set may comprise e.g.:

($P\_4\_1 > TH\_1\_4$)

wherein $P\_4\_1$ is a fourth primary parameter based on the fourth parameter data and indicative of the resistance, voltage, or current between the fourth electrode pair and $TH\_1\_4$ is a first quaternary threshold value, and wherein the first operating state is indicative of absence of fluid on the proximal side of the first adhesive layer of the base plate of the ostomy appliance. In one or more exemplary embodiments, the first quaternary threshold value $TH\_1\_4$ may correspond to an upper resistance threshold value. An upper resistance threshold value may be set to a value which is less than 30 Mega-Ohms, such as 25 Mega-Ohms, such as 20.5 Mega-Ohms, such as 20.4 Mega-Ohms.

In one or more exemplary embodiments, the following additional criterion may be determined:

($P\_1\_1 < TH\_{low}$), wherein $P\_1\_1$ is a first primary parameter based on the first parameter data, $TH\_{low}$ is a threshold value corresponding to a lower resistance threshold value. In one or more exemplary embodiments, a lower resistance threshold value may be set to a value less than 1 Mega-Ohms, such as 100 kilo-Ohms, such as 80 kilo-Ohms, such as 79 kilo-Ohms. This is indicative of a saturation of the first electrode pair by the moisture detected and there are no further changes expected by the first primary parameter. Moisture is likely to continue its progression.

In one or more exemplary embodiments, the following additional criterion may be determined:

($P\_2\_1 < TH\_{low}$), wherein $P\_2\_1$ is a second primary parameter based on the second parameter data, $TH\_{low}$ is a threshold value corresponding to a lower resistance threshold value. In one or more exemplary embodiments, a lower resistance threshold value may be set to a value less than 1 Mega-Ohms, such as 100 kilo-Ohms, such as 80 kilo-Ohms, such as 79 kilo-Ohms. This is indicative of a saturation of the second electrode pair by the moisture detected and there are no further changes expected by the second primary parameter. Moisture is likely to continue its progression.

In one or more exemplary embodiments, the following additional criterion may be determined:

(P_3_1>TH_low),

P_3_1 is a third primary parameter based on the third parameter data, and TH_low is a threshold value corresponding to a lower resistance threshold value. In one or more exemplary embodiments, a lower resistance threshold value may be set to a value less than 1 Mega-Ohms, such as 100 kilo-Ohms, such as 80 kilo-Ohms, such as 79 kilo-Ohms. This is indicative of a saturation of the third electrode pair by the moisture detected and there are no further changes expected by the second primary parameter. Moisture is likely to continue its progression.

In one or more exemplary embodiments, one or more criteria of a criteria set, e.g. one or more first criteria of the first criteria set and/or one or more second criteria of the second criteria set, may be based on timing information or one or more delay parameters based on the parameter data. In one or more exemplary embodiments, one or more delay parameters or time differences related to different parameter data, e.g. related to the first parameter data and the second parameter data, are determined.

In one or more exemplary embodiments, one or more first criteria of the first criteria set may be based on timing information (e.g. one or more delay parameters of the parameter data and/or one or more times where a parameter crosses a threshold).

In one or more exemplary embodiments, the timing information may comprise a time difference D_1_2_1 between a time T1 where P_1_1 crosses a threshold, such as TH_1_1, and a time T2 where P_2_1 crosses a threshold, such as TH_1_2. Thus, delay parameter or time difference D_1_2_1 may be given as D_1_2_1=T2−T1.

In one or more exemplary embodiments, the timing information, e.g. used in the first criteria set, may comprise a time difference D_2_3_1 between a time T2 where P_2_1 crosses a threshold, such as TH_1_2, and a time T3 where P_3_1 crosses a threshold, such as TH_1_3. Thus, delay parameter or time difference D_2_3_1 may be given as D_2_3_1=T3−T2.

In one or more exemplary embodiments, one or more criteria sets, such as the third criteria set, and/or the second criteria set, may comprise any of:

D_1_2_1>Z
D_2_3_1>Z wherein Z is a time difference constant characterizing the progression of moisture (e.g. 3 h, e.g. 2 h). Different time difference constants may be employed in different criteria sets/for different time delays.

In one or more exemplary embodiments, one or more criteria sets, such as the second criteria set, and/or the third criteria set may comprise any of:

D_1_2_1>Z wherein Z is a time difference constant characterizing the progression of moisture (e.g. 3 h, e.g. 2 h).

The second primary parameter may be indicative of the resistance between the second electrode pair (second electrode and second electrode part of the ground electrode) of the base plate.

The second parameter data may comprise a second secondary parameter, and/or a second tertiary parameter, which may be derived from the second primary parameter. A second secondary parameter may be indicative of a voltage between the second electrode pair (second electrode and second electrode part of the ground electrode) of the base plate.

The third primary parameter may be indicative of resistance between the third electrode pair (third electrode and third electrode part of the ground electrode) of the base plate. The third parameter data may comprise a third secondary parameter, and/or a third tertiary parameter, which may be derived from the third primary parameter. A third secondary parameter may be indicative of a voltage between the second electrode pair (second electrode and second electrode part of the ground electrode) of the base plate.

In one or more exemplary monitor devices, to determine an operating state of the base plate is based on a second criterion set based on the second parameter data and/or the third parameter data, wherein the operating state is determined to be the second operating state if the second criteria set is satisfied. The second criteria set may be based on the first parameter data.

The second criteria set may comprise one or more second criteria based on one or more of first parameter data, second parameter data and third parameter data. The second criteria set may comprise a second primary criterion based on the first parameter data. The second criteria set may comprise a second secondary criterion based on the second parameter data. The second criteria set may comprise a second tertiary criterion based on the third parameter data.

In one or more exemplary monitor devices, to determine an operating state of the base plate is based on a second threshold set comprising one or a plurality of second threshold values. The second threshold set may comprise one or a plurality of threshold values, e.g. to be applied in the second criteria set. The second threshold set may comprise a second primary threshold value. The second threshold set may comprise a second secondary threshold value. The second threshold set may comprise a second tertiary threshold value.

The second criteria set may be given by or at least may comprise:

(P_1_1<TH_2_1),
(P_2_1<TH_2_2), and
(P_3_1>TH_2_3)

wherein P_1_1 is a first primary parameter based on the first parameter data and indicative of the resistance between the first electrode pair, TH_2_1 is a second primary threshold value, P_2_1 is a second primary parameter based on the second parameter data and indicative of the resistance between the second electrode pair, TH_2_2 is a second secondary threshold value, P_3_1 is a third primary parameter based on the third parameter data and indicative of the resistance between the third electrode pair, TH_2_3 is a second tertiary threshold value, and wherein the second operating state is indicative of medium degree of radial erosion on the base plate. The second threshold values (TH_2_1, TH_2_2 and TH_2_3) may be the same or different, e.g. depending on the electrode configuration of the base plate. The second primary criterion (P_1_1<TH_2_1) and/or the second tertiary criterion (P_3_1>TH_2_3) may be omitted in the second criteria set.

The second operating state indicative of medium degree of radial erosion on the base plate may be indicative of a radial progression of moisture to the first electrode pair and the second electrode pair (and not the third electrode pair).

The second operating state indicative of medium degree of radial erosion on the base plate may be indicative of a radial progression of moisture to the first electrode pair and to the second electrode pair.

In one or more exemplary embodiments, when the first parameter data, the second parameter data and the third parameter data are each respectively indicative of resistance between the first electrode pair, the second electrode pair and the third electrode pair respectively, the second threshold values (TH_2_1, TH_2_2 and TH_2_3) may correspond to second resistance threshold values. In one or more exemplary embodiments, the second primary threshold value TH_2_1 may correspond to an upper resistance threshold value. An upper resistance threshold value may be set to a value which is less than 30 Mega-Ohms, such as 25 Mega-Ohms, such as 20.5 Mega-Ohms, such as 20.4 Mega-Ohms. In one or more exemplary embodiments, the second secondary threshold value TH_2_2 may correspond to the upper resistance threshold. In one or more exemplary embodiments, the second tertiary threshold value TH_2_3 may correspond to the upper resistance threshold value. In one or more exemplary embodiments, the second primary threshold value TH_2_1 may correspond to a medium resistance threshold value. A medium resistance threshold value may be set to a value less than 10 Mega-Ohms, such as 5 Mega-Ohms, such as 3 Mega-Ohms, such as 2 Mega-Ohms, such as 1 Mega-Ohms.

In one or more exemplary embodiments, when the first parameter data, the second parameter data and the third parameter data are each respectively indicative of voltage between the first electrode pair, the second electrode pair and the third electrode pair respectively, the second threshold values (TH_2_1, TH_2_2 and TH_2_3) may correspond to second voltage threshold values. In one or more exemplary embodiments, the second primary threshold value TH_2_1 may correspond to an upper voltage threshold value. An upper voltage threshold value may be set to a value less than 5 Volts, such as 3 Volts, such as 2.86 Volts. In one or more exemplary embodiments, the second secondary threshold value TH_2_2 may correspond to the upper voltage threshold value. In one or more exemplary embodiments, the second tertiary threshold value TH_2_3 may correspond to the upper voltage threshold value. In one or more exemplary embodiments, the second primary threshold value TH_2_1 may correspond to a medium voltage threshold value. A medium resistance threshold value may be set to a value less than 10 Mega-Ohms, such as 5 Mega-Ohms, such as 3 Mega-Ohms, such as 2 Mega-Ohms, such as 1 Mega-Ohms.

In one or more exemplary embodiments, the second criteria set may comprise any of:

D_1_2_1>Z wherein Z is a time difference constant characterizing the progression of moisture (e.g. 3 h, e.g. 2 h).

In one or more exemplary monitor devices, to determine an operating state of the base plate is based on a default criteria set based on the first parameter data, wherein the operating state is determined to be the default operating state if the default criteria set is satisfied, and in accordance with a determination that the operating state is the default operating state, transmit a default monitor signal comprising monitor data indicative of the default operating state of the ostomy appliance.

The default criteria set may be given by or at least may comprise:

(P_1_1>TH_D_1),
(P_2_1>TH_D_2), and
(P_3_1>TH_D_3)

wherein P_1_1 is a first primary parameter based on the first parameter data and indicative of the resistance between the first electrode pair, TH_D_1 is a default primary threshold value, P_2_1 is a second primary parameter based on the second parameter data and indicative of the resistance between the second electrode pair, TH_D_2 is a default secondary threshold value, P_3_1 is a third primary parameter based on the third parameter data and indicative of the resistance between the third electrode pair, TH_D_3 is a default tertiary threshold value, and wherein the default operating state is indicative of very low or no degree of radial erosion on the base plate. The default threshold values (TH_D_1, TH_D_2 and TH_D_3) may be the same or different, e.g. depending on the electrode configuration of the base plate. In one or more exemplary embodiments, when the first parameter data, the second parameter data and the third parameter data are each respectively indicative of resistance between the first electrode pair, the second electrode pair and the third electrode pair respectively, the default threshold values (TH_D_1, TH_D_2 and TH_D_3) may correspond to default resistance threshold values. In one or more exemplary embodiments, the second primary threshold value TH_D_1 may correspond to an upper resistance threshold value. An upper resistance threshold value may be set to a value which is less than 30 Mega-Ohms, such as 25 Mega-Ohms, such as 20.5 Mega-Ohms, such as 20.4 Mega-Ohms. In one or more exemplary embodiments, the default secondary threshold value TH_D_2 may correspond to the upper resistance threshold. In one or more exemplary embodiments, the default tertiary threshold value TH_D_3 may correspond to the upper resistance threshold value.

In one or more exemplary embodiments, when the first parameter data, the second parameter data and the third parameter data are each respectively indicative of voltage between the first electrode pair, the second electrode pair and the third electrode pair respectively, the default threshold values (TH_D_1, TH_D_2 and TH_D_3) may correspond to default voltage threshold values. In one or more exemplary embodiments, the default primary threshold value TH_D_1 may correspond to an upper voltage threshold value. An upper voltage threshold value may be set to a value less than 5 Volts, such as 3 Volts, such as 2, 86 Volts. In one or more exemplary embodiments, the default secondary threshold value TH_D_2 may correspond to the upper voltage threshold value. In one or more exemplary embodiments, the default tertiary threshold value TH_D_3 may correspond to the upper voltage threshold value.

In one or more exemplary monitor devices, to determine an operating state of the base plate is based on a third criteria set based on the third parameter data, wherein the operating state is determined to be the third operating state if the third criteria set is satisfied, and in accordance with a determination that the operating state is the third operating state, transmit a third monitor signal comprising monitor data indicative of the third operating state of the ostomy appliance.

In one or more exemplary monitor devices, the third operating state of the base plate corresponds to a situation wherein the first adhesive layer of the base plate has experienced a third degree of radial erosion, e.g. the first adhesive layer is eroded to the third radial distance of the third electrode pair.

The third criteria set may be given by or at least may comprise:

(P_1_1<TH_3_1),
(P_2_1<TH_3_2), and
(P_3_1<TH_3_3)

wherein $P\_1\_1$ is a first primary parameter based on the first parameter data and indicative of the resistance between the first electrode pair, $TH\_3\_1$ is a third primary threshold value, $P\_2\_1$ is a second primary parameter based on the second parameter data and indicative of the resistance between the second electrode pair, $TH\_3\_2$ is a third secondary threshold value, $P\_3\_1$ is a third primary parameter based on the third parameter data and indicative of the resistance between the third electrode pair, $TH\_3\_3$ is a third tertiary threshold value, and wherein the third operating state is indicative of high degree of radial erosion on the base plate. The third threshold values ($TH\_3\_1$, $TH\_3\_2$ and $TH\_3\_3$) may be the same or different, e.g. depending on the electrode configuration of the base plate. The third primary criterion ($P\_1\_1<TH\_3\_1$) and/or the third secondary criterion ($P\_2\_1<TH\_3\_2$) may be omitted in the third criteria set. The third operating state indicative of high degree of radial erosion on the base plate may be indicative of high likelihood of leakage, e.g. on the proximal side of the base plate, e.g. within a time period e.g. within the next 20 minutes. The third operating state may indicate a radial progression of moisture to the first electrode pair, the second electrode pair, and the third electrode pair.

In one or more exemplary embodiments, when the first parameter data, the second parameter data and the third parameter data are each respectively indicative of resistance between the first electrode pair, the second electrode pair and the third electrode pair respectively, the third threshold values ($TH\_3\_1$, $TH\_3\_2$ and $TH\_3\_3$) may correspond to third resistance threshold values. In one or more exemplary embodiments, the third primary threshold value $TH\_3\_1$ may correspond to an upper resistance threshold value. In one or more exemplary embodiments, the third secondary threshold value $TH\_3\_2$ may correspond to an upper resistance threshold value. In one or more exemplary embodiments, the third tertiary threshold value $TH\_3\_3$ may correspond to an upper resistance threshold value. An upper resistance threshold value may be set to a value which is less than 30 Mega-Ohms, such as 25 Mega-Ohms, such as 20.5 Mega-Ohms, such as 20.4 Mega-Ohms.

In one or more exemplary embodiments, the third primary threshold value $TH\_3\_1$ may correspond to a lower resistance threshold value. In one or more exemplary embodiments, a lower resistance threshold value may be set to a value less than 1 Mega-Ohms, such as 100 kilo-Ohms, such as 80 kilo-Ohms, such as 79 kilo-Ohms. In one or more exemplary embodiments, the third secondary threshold value $TH\_3\_2$ may correspond to a medium resistance threshold. A medium resistance threshold value may be set to a value less than 10 Mega-Ohms, such as 5 Mega-Ohms, such as 3 Mega-Ohms, such as 2 Mega-Ohms, such as 1 Mega-Ohms. In one or more exemplary embodiments, the third tertiary threshold value $TH\_3\_3$ may correspond to the upper resistance threshold. An upper resistance threshold value may be set to a value which is less than 30 Mega-Ohms, such as 25 Mega-Ohms, such as 20.5 Mega-Ohms, such as 20.4 Mega-Ohms.

In one or more exemplary embodiments, when the first parameter data, the second parameter data and the third parameter data are each respectively indicative of voltage between the first electrode pair, the second electrode pair and the third electrode pair respectively, the third threshold values ($TH\_3\_1$, $TH\_3\_2$ and $TH\_3\_3$) may correspond to third voltage threshold values. In one or more exemplary embodiments, the third primary threshold value $TH\_3\_1$ may correspond to an upper voltage threshold value. In one or more exemplary embodiments, the third secondary threshold value $TH\_3\_2$ may correspond to an upper voltage threshold value. In one or more exemplary embodiments, the second tertiary threshold value $TH\_2\_3$ may correspond to the upper voltage threshold value.

In one or more exemplary embodiments, the third primary threshold value $TH\_3\_1$ may correspond to a lower voltage threshold value. In one or more exemplary embodiments, a lower voltage threshold value may be set to a value which is less than 1 Volt, such as 0.5 Volt, such as 0.25 Volts, such as 0.22 Volts. In one or more exemplary embodiments, the third secondary threshold value $TH\_3\_2$ may correspond to a medium voltage threshold value. A medium voltage threshold value may be set to a value less than 2 Volts, such as 1.5 Volts. In one or more exemplary embodiments, the second tertiary threshold value $TH\_2\_3$ may correspond to the upper voltage threshold value.

In one or more exemplary embodiments, the third criteria set may comprise any of:
$D\_1\_2\_1<Z$
$D\_2\_3\_1<Z$
Wherein Z is a time difference constant characterizing the progression of moisture (e.g. 3 h, e.g. 2 h), a time difference $D\_1\_2\_1$ between a time T1 where $P\_1\_1$ crosses $TH\_1\_1$ and a time T2 where $P\_2\_1$ crosses $TH\_1\_2$, and a time difference $D\_2\_3\_1$ between a time T2 where $P\_2\_1$ crosses $TH\_1\_2$ and a time T3 where $P\_3\_1$ crosses $TH\_1\_3$.

In one or more exemplary monitor devices, the ostomy data comprises fourth ostomy data from a fourth electrode pair of the base plate. To apply a processing scheme may comprise to obtain fourth parameter data based on the fourth ostomy data and determine an operating state of the base plate of the ostomy appliance based on the fourth parameter data. The monitor device may be configured to, in accordance with a determination that the operating state is a fourth operating state, transmit a fourth monitor signal comprising monitor data indicative of the fourth operating state of the ostomy appliance.

In one or more exemplary monitor devices, the fourth operating state of the base plate corresponds to a situation, wherein the fourth electrode pair detects fluid, such as output, between the proximal surface of first adhesive layer and the skin of the user at a fourth radial distance, and thus there is a high risk of leakage from the ostomy appliance in the fourth operating state.

The fourth criteria set may be given by or at least may comprise:
($P\_4\_1<TH\_4\_4$)
wherein $P\_4\_1$ is a fourth primary parameter based on the fourth parameter data and indicative of the resistance between the fourth electrode pair and $TH\_4\_4$ is a fourth quaternary threshold value, and wherein the fourth operating state is indicative of high risk of leakage from the ostomy appliance.

In one or more exemplary embodiments, the fourth quaternary threshold value $TH\_4\_4$ may correspond to an upper resistance threshold value.

In one or more exemplary monitor devices, a fifth operating state of the base plate corresponds to a situation, wherein the fourth electrode pair detects fluid, such as sweat, between the proximal surface of first adhesive layer and the skin of the user at a fourth radial distance, and thus there is a no leakage from the ostomy appliance in the fifth operating state.

The fifth operating state may be determined in accordance with a determination that one or more fifth criterion of a fifth criteria set are satisfied by fourth parameter data.

The fifth criteria set may be given by or at least may comprise:

($P\_4\_1 < TH\_5\_1$)
($P\_4\_2 < TH\_5\_2$)
($P\_4\_3 < TH\_5\_3$)
($\nabla P\_4\_1 < V$)
($\nabla P\_4\_2 < V$) and
($\nabla P\_4\_3 < V$)

wherein $P\_4\_1$ is a fourth primary parameter based on the fourth parameter data and indicative of the resistance between the fourth electrode pair, $P\_4\_2$ is a fourth secondary parameter based on the fourth parameter data and indicative of the resistance between the fourth electrode and the fifth electrode, $P\_4\_3$ is a fourth tertiary parameter based on the fourth parameter data and indicative of the resistance between the fifth electrode pair and $TH\_5\_1$ is a fifth primary threshold value, $TH\_5\_2$ is a fifth secondary threshold value $TH\_5\_3$ is a fifth tertiary threshold value and $\nabla P\_4\_1$ is gradient of $P\_4\_1$, $\nabla P\_4\_2$ is gradient of $P\_4\_2$, $\nabla P\_4\_3$ is gradient of $P\_4\_3$, and V is a gradient limit (e.g. 80%). In one or more exemplary embodiments, the fifth primary threshold value $TH\_5\_1$ may correspond to an upper resistance threshold value. In one or more exemplary embodiments, $TH\_5\_2$ may correspond to an upper resistance threshold value. n one or more exemplary embodiments, $TH\_5\_3$ may correspond to an upper resistance threshold value. An upper resistance threshold value may be set to a value which is less than 30 Mega-Ohms, such as 25 Mega-Ohms, such as 20.5 Mega-Ohms, such as 20.4 Mega-Ohms. The fifth operating state may refer to presence of sweat detected by the fourth parameter data indicating moisture detected omnidirectionally from the stomal opening and uniformly.

In one or more exemplary monitor devices, a sixth operating state of the base plate corresponds to a situation, wherein the fourth electrode pair detects fluid, such as output, between the proximal surface of first adhesive layer and the skin of the user at a fourth radial distance, and thus there is a sudden leakage from the ostomy appliance in the sixth operating state.

The sixth operating state may be determined in accordance with a determination that one or more sixth criterion of a sixth criteria set are satisfied by the fourth parameter data.

The sixth criteria set may comprise a sixth primary criterion, wherein the sixth primary criterion may comprise:

($P\_4\_1 < TH\_6\_1$) and
($\nabla P\_4\_1 > V$)

The sixth criteria set may comprise a sixth secondary criterion, wherein the sixth secondary criterion may comprise:

($P\_4\_2 < TH\_6\_2$) and
($\nabla P\_4\_2 > V$)

The sixth criteria set may comprise a sixth tertiary criterion, wherein the sixth tertiary criterion may comprise:

($P\_4\_3 < TH\_6\_3$) and
($\nabla P\_4\_3 > V$)

wherein $P\_4\_1$ is a fourth primary parameter based on the fourth parameter data and indicative of the resistance between the fourth electrode pair, $P\_4\_2$ is a fourth secondary parameter indicative of the resistance between the fourth electrode and the fifth electrode, $P\_4\_3$ is a fourth tertiary parameter indicative of the resistance between the fifth electrode pair (fifth electrode and ground electrode) and $TH\_6\_1$ is a sixth primary threshold value, $TH\_6\_2$ is a sixth secondary threshold value $TH\_6\_3$ is a sixth tertiary threshold value, and $\nabla P\_4\_1$ is gradient of $P\_4\_1$, $\nabla P\_4\_2$ is gradient of $P\_4\_2$, $\nabla P\_4\_3$ is gradient of $P\_4\_3$, and V is a gradient limit (e.g. 80%). In one or more exemplary embodiments, the sixth primary threshold value $TH\_6\_1$ may correspond to an upper resistance threshold value. In one or more exemplary embodiments, $TH\_6\_2$ may correspond to an upper resistance threshold value. In one or more exemplary embodiments, $TH\_6\_3$ may correspond to an upper resistance threshold value. An upper resistance threshold value may be set to a value which is less than 30 Mega-Ohms, such as 25 Mega-Ohms, such as 20.5 Mega-Ohms, such as 20.4 Mega-Ohms. The sixth operating state may refer to presence of output detected by the fourth parameter data indicating a sudden leak, e.g. a developing leak. In one or more exemplary embodiments, when the time T is below X minutes from the placement of the base plate, where X is between 5 to 60 minutes, and when any of $P\_1\_1$, $P\_2\_1$, $P\_3\_1$ in average over T are below a default threshold value corresponding to an upper resistance threshold value, this indicates that any of the first electrode pair, the second electrode pair, and the third electrode pair is cut (e.g. cut by the user when preparing the base plate for placement around the stoma). In one or more exemplary embodiments, when the time T is below X minutes from the placement of the base plate, where X is between 5 to 60 minutes, and when any of $P\_4\_1$, $P\_4\_2$, $P\_4\_3$ in average over T are below a default threshold value corresponding to an upper resistance threshold value, this indicates an instant leakage, e.g. presence of output on the proximal side.

In one or more exemplary embodiments, any of the first criteria set, the second criteria set, the third criteria set, the fourth criteria set, the default criteria set, the fifth criteria set, the sixth criteria set may be used to define one or more further criteria sets, and thereby to determine one or more operating states.

In one or more exemplary embodiments, different criteria sets may be used to determine the same operating state.

The monitor device comprises a monitor device housing optionally made of a plastic material. The monitor device housing may be an elongate housing having a first end and a second end. The monitor device housing may have a length or maximum extension along a longitudinal axis in the range from 1 cm to 15 cm. The monitor device housing may have a width or maximum extension perpendicular to the longitudinal axis in the range from 0.5 cm to 3 cm. The monitor device housing may be curve-shaped.

The monitor device comprises a first interface. The first interface may be configured as an appliance interface for electrically and/or mechanically connecting the monitor device to the ostomy appliance. Thus, the appliance interface is configured to electrically and/or mechanically couple the monitor device and the ostomy appliance. The first interface may be configured as an accessory device interface for electrically and/or mechanically connecting the monitor device to an accessory device, such as a docking station. The first interface may be configured for coupling to a docking station of the ostomy system, e.g. for charging the monitor device and/or for data transfer between the monitor device and the docking station.

The first interface of the monitor device may comprise a plurality of terminals, such as two, three, four, five, six, seven or more terminals, for forming electrical connections with respective terminals and/or electrodes of the ostomy appliance. One or more terminals of the first interface may be configured for forming electrical connections with an accessory device, e.g. with respective terminals of a docking station. The first interface may comprise a ground terminal. The first interface may comprise a first terminal, a second terminal and optionally a third terminal. The first interface may comprise a fourth terminal and/or a fifth terminal. The first interface optionally comprises a sixth terminal. In one or more exemplary monitor devices, the first interface has M terminals, wherein M is an integer in the range from 4 to 8.

The first interface of the monitor device may comprise a coupling part for forming a mechanical connection, such as a releasable coupling between the monitor device and the base plate. The coupling part and the terminals of the first interface form (at least part of) a first connector of the monitor device.

The monitor device comprises a power unit for powering the monitor device. The power unit may comprise a battery. The power unit may comprise charging circuitry connected to the battery and terminals of the first interface for charging the battery via the first interface, e.g. the first connector. The first interface may comprise separate charging terminal(s) for charging the battery.

The monitor device may comprise a sensor unit with one or more sensor. The sensor unit is connected to the processor for feeding sensor data to the processor. The sensor unit may comprise an accelerometer for sensing acceleration and provision of acceleration data to the processor. The sensor unit may comprise a temperature sensor for provision of temperature data to the processor.

The monitor device comprises a second interface connected to the processor. The second interface may be configured as an accessory interface for connecting, e.g. wirelessly connecting, the monitor device to one or more accessory devices. The second interface may comprise an antenna and a wireless transceiver, e.g. configured for wireless communication at frequencies in the range from 2.4 to 2.5 GHz. The wireless transceiver may be a Bluetooth transceiver, i.e. the wireless transceiver may be configured for wireless communication according to Bluetooth protocol, e.g. Bluetooth Low Energy, Bluetooth 4.0, Bluetooth 5. The second interface optionally comprises a loudspeaker and/or a haptic feedback element for provision of an audio signal and/or haptic feedback to the user, respectively.

In one or more exemplary ostomy systems, the monitor device forms an integrated part of the ostomy appliance, e.g. the monitor device may form an integrated part of a base plate of the ostomy appliance.

The ostomy system may comprise a docking station forming an accessory device of the ostomy system. The docking station may be configured to electrically and/or mechanically couple the monitor device to the docking station.

The docking station may comprise a docking monitor interface. The docking monitor interface may be configured for electrically and/or mechanically connecting the monitor device to the docking station. The docking monitor interface may be configured for wirelessly connecting the monitor device to the docking station. The docking monitor interface of the docking station may be configured to electrically and/or mechanically couple the docking station and the monitor device.

The docking monitor interface of the docking station may comprise, e.g. as part of a first connector of the docking monitor interface, a coupling part for forming a mechanical connection, such as a releasable coupling between the monitor device and the docking station. The coupling part may be configured to engage with a coupling part of the monitor device for releasably coupling the monitor device to the docking station.

The docking monitor interface of the docking station may comprise, e.g. as part of a first connector of the docking monitor interface, a plurality of terminals, such as two, three, four, five, six, seven or more terminals, for forming electrical connections with respective terminals of the monitor device. The docking monitor interface may comprise a ground terminal. The docking monitor interface may comprise a first terminal and/or a second terminal. The docking station may comprise a third terminal. The docking monitor interface may comprise a fourth terminal and/or a fifth terminal. The docking monitor interface optionally comprises a sixth terminal.

Disclosed is a monitor device for an ostomy system. The monitor device comprises a processor; memory; and a first interface connected to the processor and the memory. The first interface comprises: a plurality of terminals including a first terminal and a second terminal, the first terminal configured to form an electrical connection with a first electrode of an ostomy appliance of the ostomy system and the second terminal configured to form an electrical connection with a second electrode of the ostomy appliance; and a data collector coupled to the first terminal and the second terminal. The first electrode and the second electrode of the ostomy appliance may indicate different characteristics of the ostomy appliance. For example, the first electrode may indicate the quality of adhesion between the ostomy appliance and a skin surface of a user and the second electrode may indicate the presence or absence of a leak of output between the ostomy appliance and the skin surface of a user. As such, the data received by the data collector via the first and second terminals may indicate different characteristics of the ostomy appliance.

The data collector comprises a data collection unit and a data collection controller. The data collection controller is configured to: collect data from the plurality of terminals according to a primary data collection scheme; and collect data from the plurality of terminals according to a secondary data collection scheme, wherein the primary data collection scheme is different from the secondary data collection scheme. In particular, the data collection controller may send one or more control signals, via a first control pin, to the data collection unit to collect data according to different data collection schemes (e.g., the primary data collection scheme or the secondary data collection scheme). The data collected by the data collection unit may be transmitted from the data collection unit to the data collection controller via first primary and secondary data pins. As stated above, the different terminals may indicate different characteristics of the ostomy appliance. As such, it may be beneficial to collect data of the different characteristics according to different data collection schemes.

In embodiments, the control signal(s) sent to the data collection unit may be in response to one or more control signals from the processor. In particular, the processor may send one or more control signals, via a second control pin, to the data collection controller and, in response, the data collection controller may send one or more control signals, via the first control pin, to the data collection unit. In addition, the data transmitted from the data collection unit to the data collection controller via the first primary and secondary data pins may be transmitted from the data collection controller to the processor via the second primary and secondary data pins. The processor may then store the data collected in memory.

The data collector unit may include one or more analog-to-digital converters (ADC). The ADC may receive signals via the terminals and convert the signals from the analog domain (e.g., voltage) to the digital domain (e.g., digital signal). In embodiments, the signal acquisition range of the ADC may be controlled by a control signal sent from the data collection controller to the data collection unit via the first control pin. The signal acquisition range of the ADC may be adapted in response to one or more control signals in order to optimize a signal-to-noise ratio of any signals received via the terminals. Additionally or alternatively, the ADC may be adapted in response to which of the terminals data is being collected. For example, the ADC may be adapted in response to which of the first, second, and/or third resistive pairs data is being collected.

In embodiments, the sampling rate of the primary data collection scheme may be different than a sampling rate of the secondary data collection scheme. For example, the data collection unit may sample the resistance between the first resistive pair, the second resistive pair, the third resistive pair, and/or between two sensor points via one or more of the terminals and the sampling rate of the samples may be different depending on whether the primary data collection scheme is implemented or the secondary data collection scheme is implemented. That is, the sampling rate of the primary data collection scheme may be at a first sampling rate and the sampling rate of the secondary collection scheme may be at a second sampling rate such that the first sampling rate is different than the second sampling rate. For example, the primary data collection scheme may include a sampling rate between 0.01 Hz to 0.5 kHz and the secondary data collection scheme may comprise a sampling rate between 0.1 Hz to 1.0 kHz. By collecting data at different sampling rates, characteristics of the ostomy appliance that are more likely to change quickly can be more frequently monitored while characteristics that are less likely to change quickly can be less frequently monitored. As such, the longevity of a power unit supplying power to the monitor device may be increased and/or storage of the memory on which the data corresponding to the characteristics may be better utilized.

Additionally or alternatively, the primary data collection scheme may differ from the secondary data collection scheme by their respective number of samples per measurement. That is, each measurement saved to memory may be comprised of a number of samples (e.g., the sampled resistance between the first resistive pair, the second resistive pair, the third resistive pair, and/or between two sensor points). And, the number of samples per measurement may differ depending on whether the primary data collection scheme is implemented, or the secondary data collection scheme is implemented. That is, a measurement of the primary data collection scheme may include a first number of samples and a measurement of the secondary data collection scheme may include a second number of samples such that the first number of samples is different than the second number of samples. For example, the primary data collection scheme may comprise ten (10) samples to a measurement and the secondary data collection scheme may comprise one hundred (100) samples to a measurement.

Additionally or alternatively, the primary data collection scheme may differ from the secondary data collection scheme by their respective measurement rates. In particular, each measurement may be comprised of one or more samples (e.g., the sampled resistance between the first resistive pair, the second resistive pair, the third resistive pair, and/or between two sensor points). And, the measurement rates may differ depending on whether the primary data collection scheme is implemented, or the secondary data collection scheme is implemented. That is, the measurement rate of the primary data collection scheme may be at a first measurement rate and the measurement rate of the secondary collection scheme may be at a second measurement rate such that the first measurement rate is different than the second measurement rate. For example, the primary data collection scheme may include a measurement rate at 50 Hz and the secondary data collection scheme may comprise a measurement rate at 10 Hz.

The data collection controller may be configured to select the data collection scheme based on a control signal indicative of the data collection scheme from the processor. In embodiments, the processor may be monitoring characteristics of the ostomy appliance, accessory device, user, and/or environment of the user and, based on these characteristics, the processor may instruct the data collection controller to select a specific data collection scheme. Examples of characteristics the processor may be monitoring include but are not limited to the following.

The processor may be configured to determine the control signal based on an operating state of the ostomy appliance.

The processor may be configured to determine the control signal in accordance with an orientation of the user.

The processor may be configured to determine the control signal in accordance with an activity level of a user.

The processor may be configured to determine the control signal in accordance with a distance between the controller and an accessory device.

The processor may be configured to determine the control signal in accordance with a power capacity of a power unit of the monitor device.

The processor may be configured to determine the control signal in accordance with a model type of the ostomy appliance.

The processor may be configured to determine the control signal in accordance with a wear time of the ostomy appliance.

The processor may be configured to determine the control signal in accordance with preferences of a user of the ostomy appliance.

The processor may be configured to determine the control signal in accordance with a location of a user of the ostomy appliance.

The processor may be configured to determine the control signal based on if a user cuts, for example, a resistive pair.

The processor may be configured to determine the control signal based on the wetting of a resistive pair.

Also disclosed is a method for data collection from an ostomy appliance. The method comprises collecting data from a first terminal and a second terminal according to a primary data collection scheme, the first terminal forming an electrical connection with a first electrode of an ostomy appliance and the second terminal forming an electrical connection with a second electrode of an ostomy appliance. Similar to as stated above, the different terminals may indicate different characteristics of the ostomy appliance.

The method further comprises collecting data from the first terminal and the second terminal according to a secondary data collection scheme, wherein the primary data collection scheme is different from the secondary data collection scheme. Due to the different terminals indicating different characteristics of the ostomy appliance, it may be beneficial to collect data of the different characteristics according to different data collection schemes.

In embodiments, a sampling rate of the primary data collection scheme may be different from a sampling rate of the secondary data collection scheme. By collecting data at different sampling rates, characteristics of the ostomy appliance that are more likely to change quickly can be more frequently monitored while characteristics that are less likely to change quickly can be less frequently monitored. As such, the longevity of a power unit supplying power to the monitor device may be increased and/or storage of the memory on which the data corresponding to the characteristics may be better utilized.

In embodiments, the method may comprise selecting the data collection scheme in accordance with an operating state of the ostomy appliance. In embodiments, characteristics of the ostomy appliance may be monitored (e.g., the operating state of the ostomy appliance) and, based on these characteristics, it may be beneficial to select a specific data collection scheme based on, potentially different operating states.

FIG. 1 illustrates an exemplary ostomy system. The ostomy system 1 comprises an ostomy appliance 2 including a base plate 4 and an ostomy pouch (not shown). Further, the ostomy system 1 comprises a monitor device 6 and an accessory device 8 (mobile telephone). The monitor device 6 is connectable to the base plate 4 via respective first connectors of the monitor device 6 and base plate 4. The monitor device 6 is configured for wireless communication with the accessory device 8. Optionally, the accessory device 8 is configured to communicate with a server device 10 of the ostomy system 1, e.g. via network 12. The server device 10 may be operated and/or controlled by the ostomy appliance manufacturer and/or a service centre. Ostomy data or parameter data based on the ostomy data are obtained from electrodes/sensors of the ostomy appliance 2 with the monitor device 6. The monitor device 6 processes the ostomy data and/or parameter data based on the ostomy data to determine monitor data that are transmitted to the accessory device 8. In the illustrated ostomy system, the accessory device 8 is a mobile phone, however the accessory device 8 may be embodied as another handheld device, such as a tablet device, or a wearable, such as a watch or other wrist-worn electronic device. Accordingly, the monitor device 6 is configured to determine and transmit monitor data to the accessory device 8. The base plate 4 comprises a coupling member 14 in the form of a coupling ring 16 for coupling an ostomy pouch (not shown) to the base plate (two-part ostomy appliance). The base plate 4 has a stomal opening 18 with a center point 19. The size and/or shape of the stomal opening 18 is typically adjusted by the user or nurse before application of the ostomy appliance to accommodate the user's stoma.

The ostomy system 1 optionally comprises a docking station 20 forming an accessory device of the ostomy system 1. The docking station comprises 20 comprises a docking monitor interface including a first connector 22 configured for electrically and/or mechanically connecting the monitor device 6 to the docking station 20. The docking monitor interface may be configured for wirelessly connecting the monitor device to the docking station. The docking station 20 comprises a user interface 24 for receiving user input and/or providing feedback to the user on the operational state of the docking station 20. The user interface 24 may comprise a touch-screen. The user interface 24 may comprise one or more physical buttons and/or one or more visual indicators, such as light emitting diodes.

A user interface refers herein to a graphical representation comprising a collection of user interface objects. A user interface comprises one or more user interface objects. A user interface may be referred to as a user interface screen.

A user interface object refers herein to a graphical representation of an object that is displayed on the display of the accessory device. The user interface object may be user-interactive, or selectable by a user input. For example, an image (e.g., icon), a button, and text (e.g., hyperlink) each optionally constitute a user interface object. The user interface object may form part of a widget. A widget may be a mini-application that may be used by the user and created by the user. A user interface object may comprise a prompt, application launch icon, and/or an action menu. An input, such as first input and/or second input, may comprise a touch (e.g. a tap, a force touch, a long press), a and/or movement of contact (e.g. a swipe gesture, e.g. for toggling). The movement on contact may be detected by a touch sensitive surface, e.g. on a display of an accessory device. Thus, the display may be a touch sensitive display. An input, such as first input and/or second input, may comprise a lift off. An input, such as first input and/or second input, may comprise a touch and a movement followed by a lift off.

The display of the accessory device may be configured to detect touch (e.g. the display is a touch-sensitive display), the input comprises a contact on the touch sensitive display. A touch-sensitive display provides an input interface and an output interface between the accessory device and a user. A processor of the accessory device may be configured to receive and/or send electrical signals from/to touch-sensitive display. A touch-sensitive display is configured to display visual output to the user. The visual output optionally includes graphics, text, icons, video, and any combination thereof (collectively termed "graphics"). For example, some or all of the visual output may be seen as corresponding to user-interface objects.

The processor of the accessory device may be configured to display, on the display, one or more user interfaces, such as user interface screens, including a first user interface and/or a second user interface. A user interface may comprise one or more, such as a plurality of user interface objects. For example, the first user interface may comprise a first primary user interface object and/or a first secondary user interface object. A second user interface may comprise a second primary user interface object and/or a second secondary user interface object. A user interface object, such as the first primary user interface object and/or the second primary user interface object, may represent an operating state of the base plate.

Figure 2:
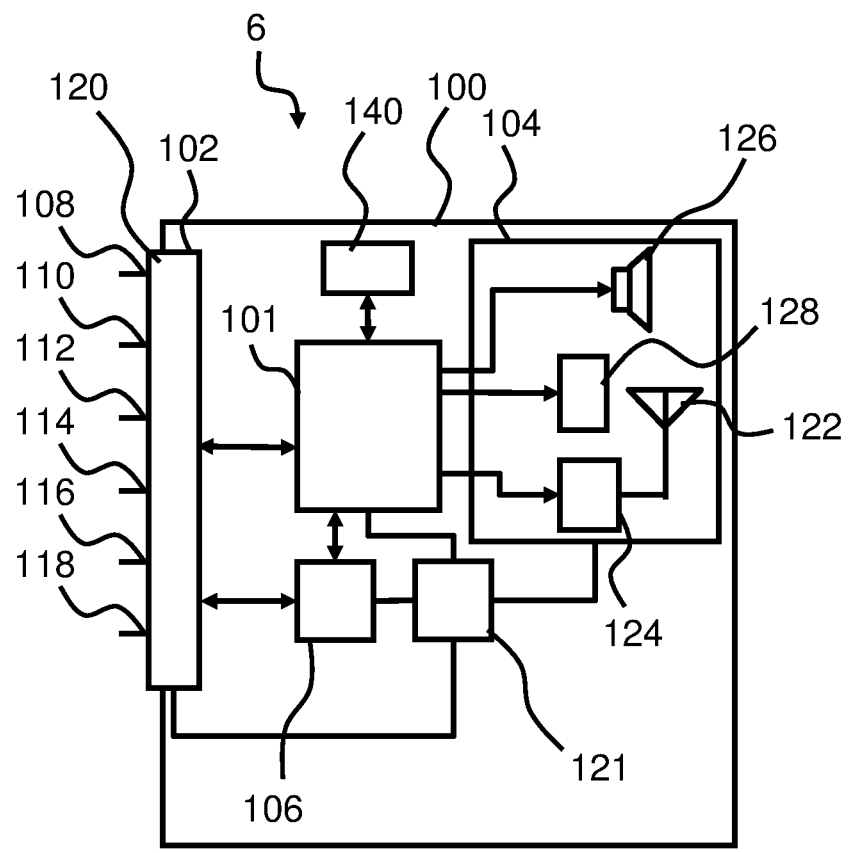
FIG. 2 illustrates an exemplary monitor device of the ostomy system.

FIG. 2 is a schematic block diagram of an exemplary monitor device. The monitor device 6 comprises a monitor device housing 100, a processor 101 and one or more interfaces, the one or more interfaces including a first interface 102 (appliance interface) and a second interface 104 (accessory interface). The monitor device 6 comprises a memory 106 for storing ostomy data and/or parameter data based on the ostomy data. The memory 106 is connected to the processor 101 and/or the first interface 102.

The first interface 102 is configured as an appliance interface for electrically and/or mechanically connecting the monitor device 6 to the ostomy appliance, e.g. ostomy appliance 2. The first interface 102 comprises a plurality of terminals for forming electrical connections with respective terminals of the ostomy appliance 2 (base plate 4). The first interface 102 comprises a ground terminal 108, a first terminal 110, a second terminal 112 and a third terminal 114. The first interface 102 optionally comprises a fourth terminal 116 and a fifth terminal 118. The first interface 102 of the monitor device 6 comprises a coupling part 120 for forming a mechanical connection, such as a releasable coupling between the monitor device and the base plate. The coupling part 120 and the terminals 108, 110, 112, 114, 116, and 118 of the first interface 102 form (at least part of) a first connector of the monitor device 6.

The monitor device 6 comprises a power unit 121 for powering the monitor device and active components thereof, i.e. the power unit 121 is connected to the processor 101, the first interface 102, the second interface 104, and memory 106. The power unit comprises a battery and charging circuitry. The charging circuitry is connected to the battery and terminals of the first interface 102 for charging the battery via terminals of the first interface, e.g. terminals of the first connector.

The second interface 104 of monitor device is configured as an accessory interface for connecting the monitor device 6 to one or more accessory devices such as accessory device 8. The second interface 104 comprises an antenna 122 and a wireless transceiver 124 configured for wireless communication with accessory device(s). Optionally, the second interface 104 comprises a loudspeaker 126 and/or a haptic feedback element 128 for provision of respective audio signal and/or haptic feedback to the user.

The monitor device 6 optionally comprises a sensor unit 140 connected to the processor 101. The sensor unit 140 comprises a temperature sensor for feeding temperature data to the processor and/or a G-sensor or accelerometer for feeding acceleration data to the processor 101.

The processor 101 is configured to apply a processing scheme, and the first interface 102 is configured for collecting ostomy data from the base plate coupled to the first interface, the ostomy data comprising first ostomy data from a first electrode pair of the base plate, second ostomy data from a second electrode pair of the base plate, and third ostomy data from a third electrode pair of the base plate. The ostomy data may be stored in the memory 106 and/or processed in the processor 101 in order to obtain parameter data. The parameter data may be stored in the memory 106. The processor 101 is configured to apply a processing scheme, wherein to apply a processing scheme comprises obtain first parameter data based on the first ostomy data; obtain second parameter data based on the second ostomy data; obtain third parameter data based on the third ostomy data. In other words, the processor 101 is configured to obtain first, second and third parameter data based on respective first, second and third ostomy data. To apply a processing scheme comprises to determine an operating state of the base plate of the ostomy appliance based on one or more, e.g. all, of the first parameter data, the second parameter data and the third parameter data, wherein the operating state is indicative of a degree of radial erosion of the base plate and/or acute leakage risk for the ostomy appliance. The monitor device 6 is configured to, in accordance with a determination that the operating state is a first operating state, transmit a first monitor signal comprising monitor data indicative of the first operating state of the base plate via the second interface; and in accordance with a determination that the operating state is a second operating state, transmit a second monitor signal comprising monitor data indicative of the second operating state of the base plate via the second interface.

The monitor device 100 is configured to obtain ostomy data from the base plate coupled to the first interface 102. The ostomy data may be stored in the memory 106 and/or processed in the processor 101 in order to obtain parameter data based on the ostomy data.

Figure 3:
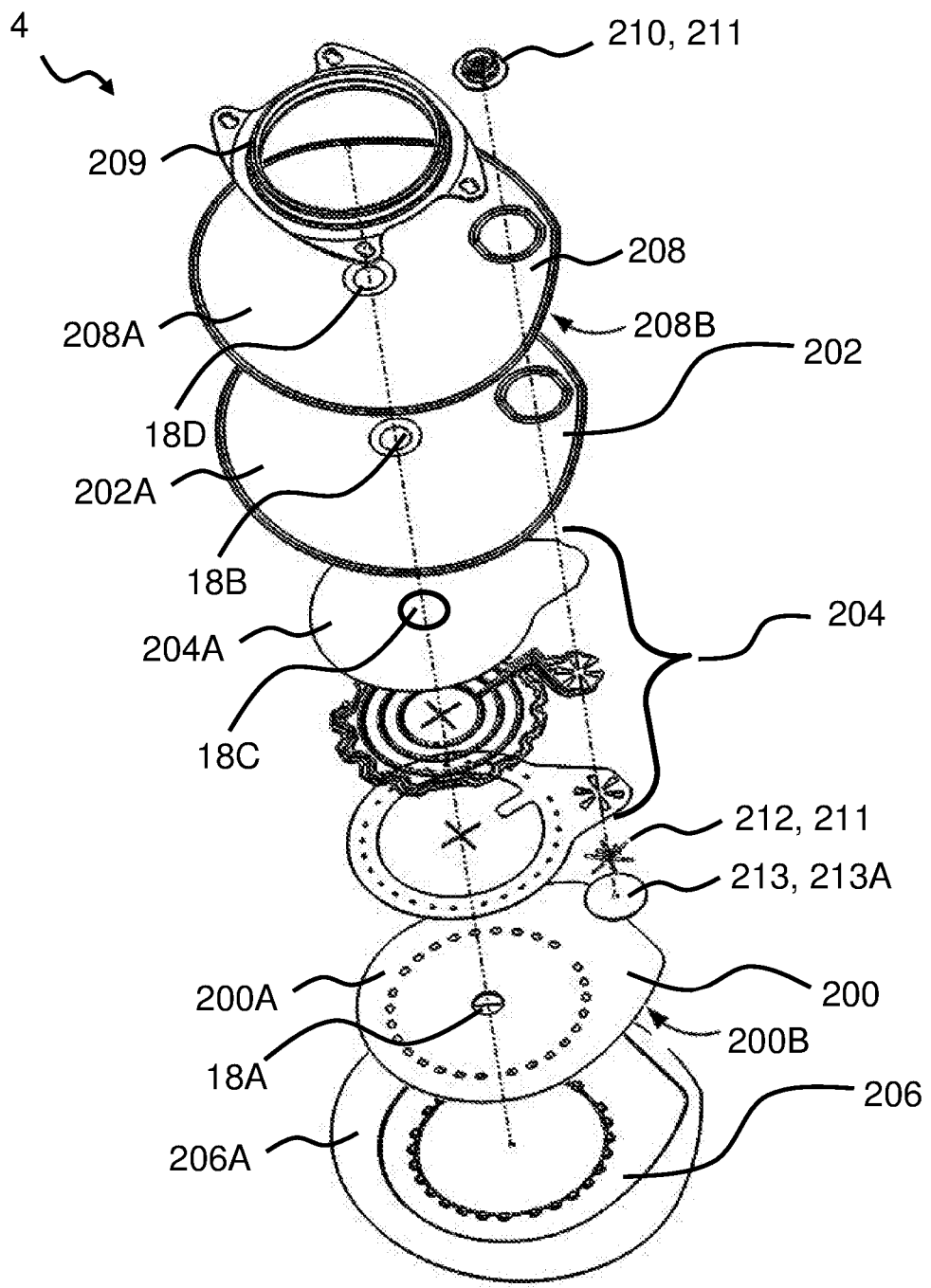
FIG. 3 is an exploded view of a base plate of an ostomy appliance.

FIG. 3 illustrates an exploded view of an exemplary base plate of an ostomy appliance. The base plate 4 comprises a first adhesive layer 200 with a stomal opening 18A. During use, a proximal surface of the first adhesive layer 200 adheres to the user's skin in the peristomal area and/or to additional seals, such as sealing paste, sealing tape and/or sealing ring. The base plate 4 optionally comprises a second adhesive layer 202, also denoted rim adhesive layer. The base plate 4 comprises a plurality of electrodes arranged in an electrode assembly 204. The electrode assembly 204 is arranged between the first adhesive layer 200 and the second adhesive layer 202 with a stomal opening 18B. The electrode assembly 204 comprises a support layer with stomal opening 18C and electrodes formed on a proximal surface of the support layer. The base plate 4 comprises a release liner 206 that is peeled off by the user prior to applying the base plate 4 on the skin. The base plate 4 comprises a top layer 208 with a stomal opening 18D and a coupling ring 209 for coupling an ostomy pouch to the base plate 4. The top layer 208 is a protective layer protecting the second adhesive layer 202 from external strains and stress during use.

The base plate 4 comprises a monitor interface. The monitor interface is configured for electrically and/or mechanically connecting the ostomy appliance (base plate 4) to the monitor device. The monitor interface of the base plate comprises a coupling part 210 for forming a mechanical connection, such as a releasable coupling between the monitor device and the base plate. The coupling part 210 is configured to engage with a coupling part of the monitor device for releasably coupling the monitor device to the base plate 4. Further, the monitor interface of the base plate 4 comprises a plurality of terminal elements respectively forming a plurality of terminals 212 for forming electrical connections with respective terminals of the monitor device. The coupling part 210 and the terminals 212 form a first connector 211 of the base plate 4. The base plate 4 comprises a first intermediate element 213 on the distal side of the electrode assembly. The first intermediate element 213 is arranged between the terminal elements forming terminals 212 and the first adhesive layer (not shown). The first intermediate element 213 covers the terminal elements forming terminals 212 of the base plate 4 when seen in the axial direction and protects the first adhesive layer from mechanical stress from the terminal elements of the base plate.

Figure 4:
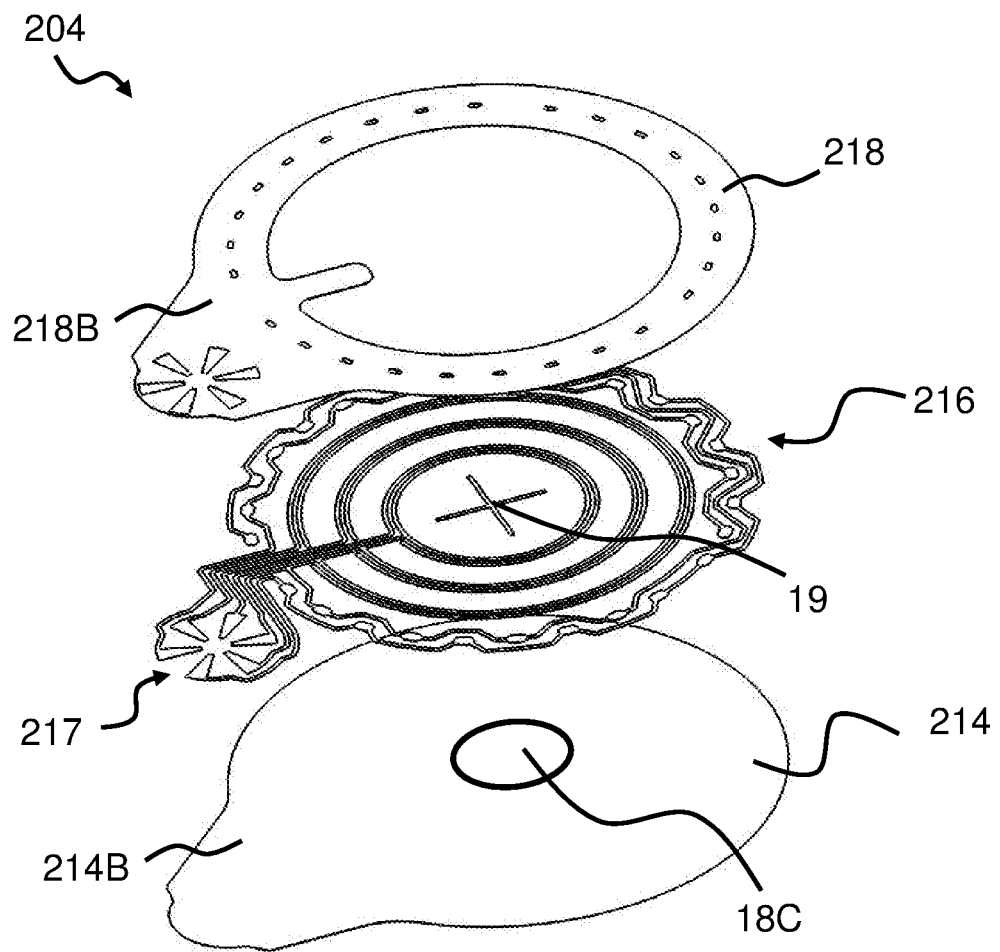
FIG. 4 is an exploded view of an exemplary electrode assembly.

FIG. 4 illustrates an exploded view of an exemplary electrode assembly 204 of a base plate. The electrode assembly 204 has a distal side 204A and a proximal side 204B. The electrode assembly 204 comprises a support layer 214 with proximal surface 214B and electrodes 216 arranged on the proximal side of the support layer 214 and including a ground electrode, a first electrode, a second electrode, a third electrode, a fourth electrode, and a fifth electrode, wherein each electrode has a respective connection part 217 for connecting the electrodes 216 to respective terminal elements of the monitor interface. The electrodes 216 are positioned and/or formed on a proximal side 214B of the support layer 214. Further, electrode assembly 204 comprises a masking element 218 with proximal surface 218B and configured to insulate electrode parts of electrodes 216 from the first adhesive layer of the base plate. The masking element 218 covers or overlap with parts of the electrodes 216 when seen in the axial direction.

Figure 5:
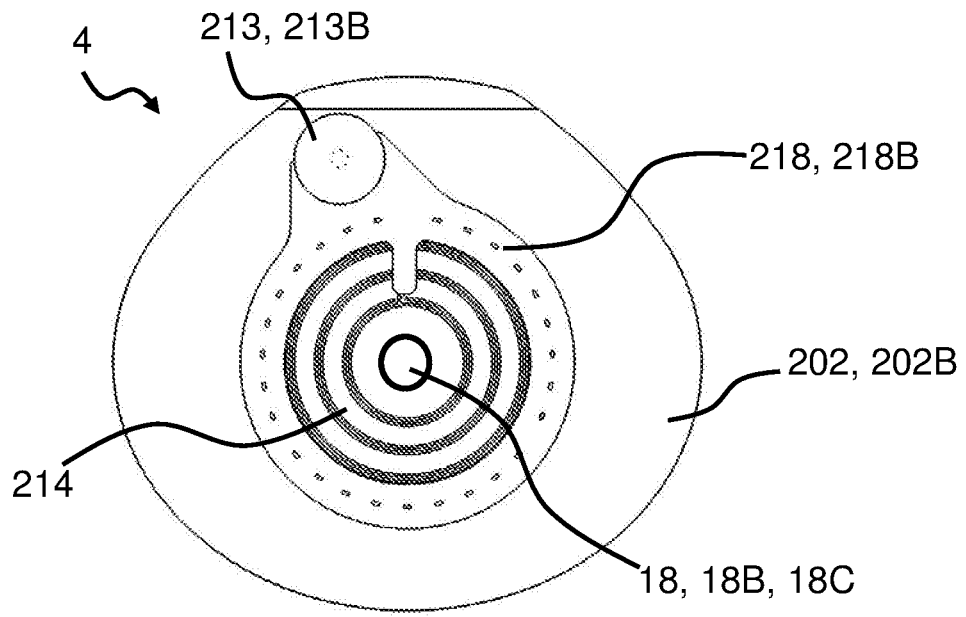
FIG. 5 is a proximal view of parts of a base plate.

FIG. 5 is a proximal view of proximal surfaces of base plate parts of the base plate without the first adhesive layer and the release liner. The base plate 4 comprises a first intermediate element 213 on the distal side of the electrode assembly, i.e. between the electrode assembly 204 and the first adhesive layer (not shown). The first intermediate element 213 covers the terminal elements of the base plate 4 when seen in the axial direction and protects the first adhesive layer from mechanical stress from the terminal elements of the base plate.

Figure 6:
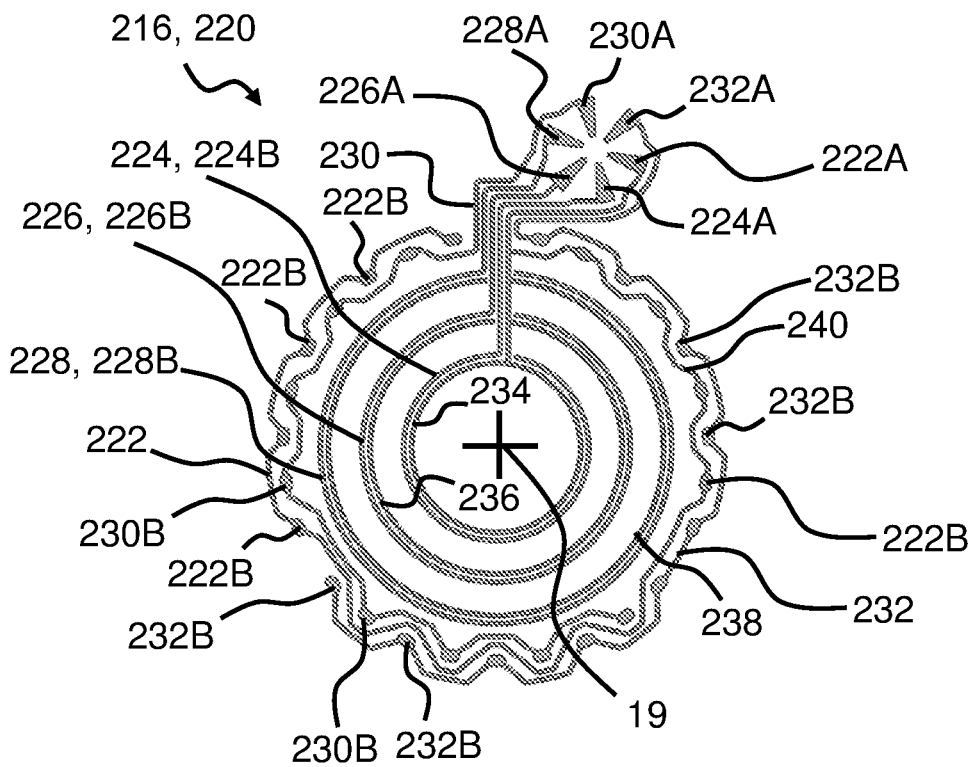
FIG. 6 is a distal view of an exemplary electrode configuration.

FIG. 6 is a distal view of an exemplary electrode configuration 220 of electrodes 216 of the electrode assembly 204. The electrode configuration 220/electrode assembly 204 comprises a ground electrode 222, a first electrode 224, a second electrode 226, a third electrode 228, a fourth electrode 230, and a fifth electrode 232. The ground electrode 222 comprises a ground connection part 222A and the first electrode 224 comprises a first connection part 224A. The second electrode 226 comprises a second connection part 226A and the third electrode 228 comprises a third connection part 228A. The fourth electrode 230 comprises a fourth connection part 230A and the fifth electrode 232 comprise a fifth connection part 232A.

The fourth electrode 230 comprises fourth sensing parts 230B. The fifth electrode 232 comprises fifth sensing parts 232B.

The ground electrode 222 comprises a first electrode part 234 for forming a ground or reference for the first electrode 224. The ground electrode 222 comprises a second electrode part 236 for forming a ground or reference for the second electrode 226. The ground electrode 222 comprises a third electrode part 238 for forming a ground or reference for the third electrode 228. The masking element 218 is arranged proximal to the electrodes 222, 224, 226, 228 covering and insulating parts of the electrodes from the first adhesive and forming respective conductor parts of the electrodes 222, 224, 226, 228. The parts of the electrodes 222, 224, 226, 228 not covered by the masking element 219 contacts the first adhesive layer and form sensing parts 224B, 226B, 228B of electrodes 224, 226, 228, respectively. Further, the electrode parts 234, 236, 238 form sensing parts of the ground electrode 222.

The first sensing part 224B extends circularly at least 330 degrees around the stomal opening at a first radial distance R1 from the center point 19. The first radial distance R1 is 14 mm. The first electrode part 234 is arranged on the inside of the first sensing part (i.e. closer to the center point) and extends circularly at least 330 degrees around the stomal opening at a first ground distance RG1 from the first sensing part (radially from the center point). The first ground distance RG1 between sensing part of first electrode and first electrode part is about 1 mm.

The second sensing part 226B extends circularly at least 330 degrees around the stomal opening at a second radial distance R2 from the center point 19. The second radial distance R2 is 18 mm. The second electrode part 236 is arranged on the inside of the second sensing part 226B (i.e. closer to the center point) and extends circularly at least 330 degrees around the stomal opening at a second ground distance RG2 from the second sensing part 226B (radially from the center point). The second ground distance RG2 between sensing part of second electrode and second electrode part is about 1 mm.

The third sensing part 228B extends circularly at least 330 degrees around the stomal opening at a third radial distance R3 from the center point 19. The third radial distance R3 is about 26 mm. The third electrode part 238 is arranged on the inside of the third sensing part 228B (i.e. closer to the center point) and extends circularly at least 330 degrees around the stomal opening at a third ground distance RG3 from the third sensing part 228B (radially from the center point). The third ground distance RG3 between sensing part of third electrode and third electrode part is about 1 mm.

The ground electrode 222 comprises a fourth electrode part 240 for forming a ground or reference for the fourth electrode 230 and the fifth electrode 232. The fourth electrode part 240 of the ground electrode 222 extends at least 300 degrees around the stomal opening and comprises ground sensing parts 222B. The fourth sensing parts 230B, fifth sensing parts 232B, and ground sensing parts of the fourth electrode part 240 are circularly distributed around the center point 19 at a leakage radius from the center point. The fourth sensing parts 230B, fifth sensing parts 232B, and ground sensing parts of the fourth electrode part may have a radial extension larger than 1.0 mm, such as in the range from 1.5 mm to 3.0 mm, e.g. about 2.0 mm. The fourth sensing parts 230B, fifth sensing parts 232B, and ground sensing parts of the fourth electrode part 240 may have a circumferential extension (perpendicular to the radial extension) larger than 1.0 mm, such as in the range from 2.5 mm to 5.0 mm, e.g. about 3.5 mm.

The ground electrode 222 comprises a first electrode part 234 for forming a ground for the first electrode 224. The ground electrode 222 comprises a second electrode part 236 for forming a ground for the second electrode 226. The ground electrode 222 comprises a third electrode part 238 for forming a ground for the third electrode 228. The ground electrode 222 comprises a fourth electrode part 240 for forming a ground for the fourth electrode 230 and the fifth electrode 232. The fourth electrode part 240 of the ground electrode 222 comprises ground sensing parts 222B.

Figure 7:
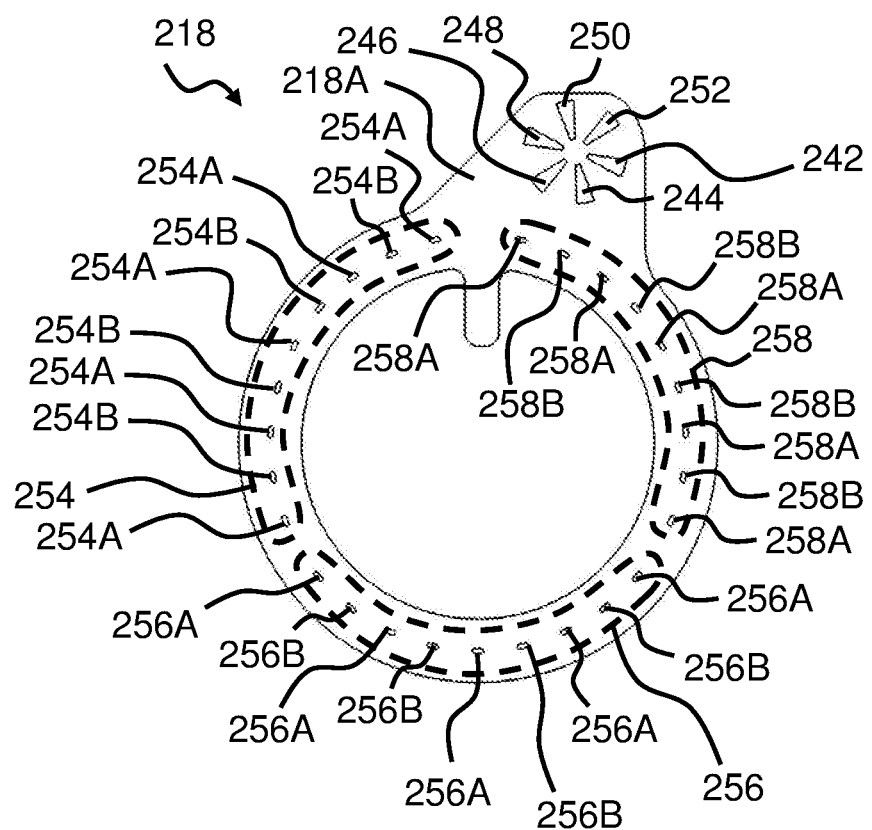
FIG. 7 is a distal view of an exemplary masking element.

FIG. 7 is a distal view of an exemplary masking element. The masking element 218 optionally has a plurality of terminal openings including six terminal openings. The plurality of terminal openings comprises a ground terminal opening 242, a first terminal opening 244, a second terminal opening 246, a third terminal opening 248, a fourth terminal opening 250, and a fifth terminal opening 252. The terminal openings 242, 244, 246, 248, 250, 252 of the masking element 218 are configured to overlap and/or be aligned with respective connection parts 222A, 224A, 226A, 228A, 230A, 232A of the electrodes of the electrode assembly.

The masking element 218 has a plurality of sensor point openings. The sensor point openings comprise primary sensor point openings shown within dotted line 254, each primary sensor point opening configured to overlap a part of the ground electrode 222 and/or a part of the fourth electrode 230. The primary sensor point openings 254 comprise, in the illustrated exemplary masking element, five primary first sensor point openings 254A each configured to overlap a part of the ground electrode 222. The primary sensor point openings 254 comprise, in the illustrated exemplary masking element, four primary second sensor point openings 254B each configured to overlap a part of the fourth electrode 230. The sensor point openings comprise secondary sensor point openings shown within dotted line 256, each second sensor point opening configured to overlap a part of the fourth electrode 230 and/or a part of the fifth electrode 232. The secondary sensor point openings 256 comprise, in the illustrated exemplary masking element, five secondary first sensor point openings 256A each configured to overlap a part of the fifth electrode 232. The secondary sensor point openings 256 comprise, in the illustrated exemplary masking element, four secondary second sensor point openings 256B each configured to overlap a part of the fourth electrode 230. The sensor point openings comprise tertiary sensor point openings shown within dotted line 258, each tertiary sensor opening configured to overlap a part of the fifth electrode 232 and/or a part of the ground electrode 222. The tertiary sensor point openings 258 comprise, in the illustrated exemplary masking element, five tertiary first sensor point openings 258A each configured to overlap a part of the fifth electrode 232. The tertiary sensor point openings 258 comprise, in the illustrated exemplary masking element, four tertiary second sensor point openings 258B each configured to overlap a part of the ground electrode 222.

Figure 8:
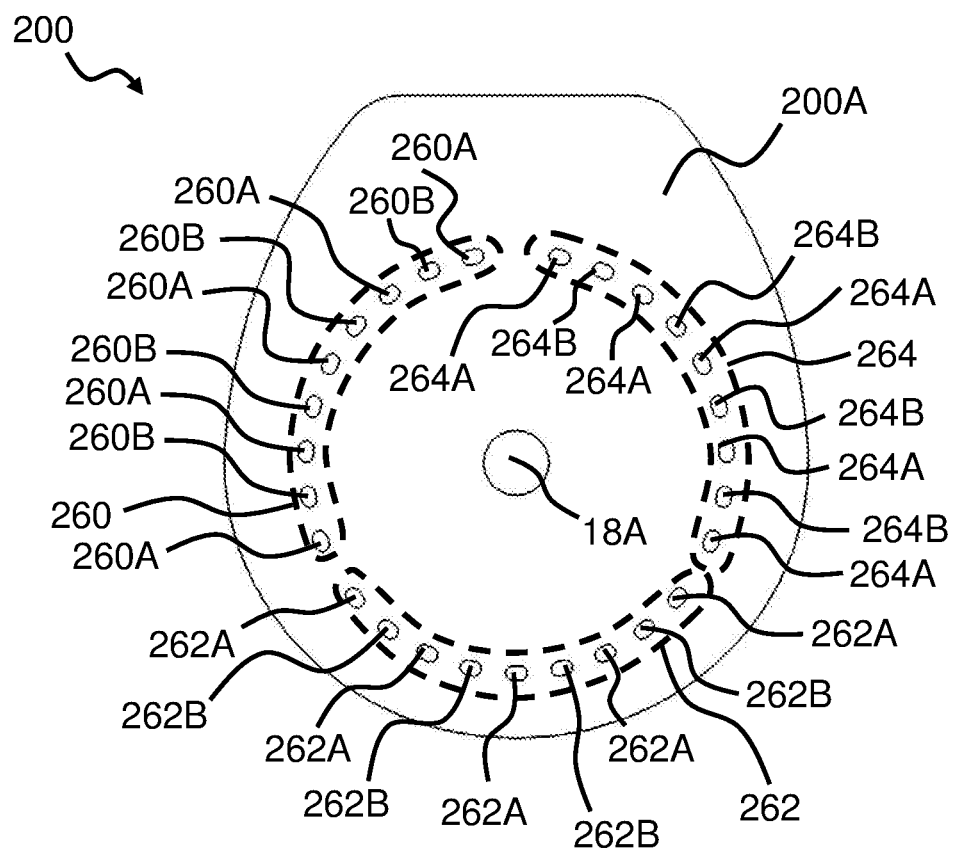
FIG. 8 is a distal view of an exemplary first adhesive layer.

FIG. 8 is a distal view of an exemplary first adhesive layer. The first adhesive layer 200 has a plurality of sensor point openings. The sensor point openings of the first adhesive layer comprise primary sensor point openings shown within dotted line 260, each primary sensor point opening configured to overlap a part of the ground electrode 222 and/or a part of the fourth electrode 230 of the electrode assembly. The primary sensor point openings 260 comprise, in the illustrated exemplary first adhesive layer, five primary first sensor point openings 260A each configured to overlap a part of the ground electrode 222. The primary sensor point openings 260 comprise, in the illustrated exemplary first adhesive layer, four primary second sensor point openings 260B each configured to overlap a part of the fourth electrode 230. The sensor point openings of the first adhesive layer comprise secondary sensor point openings shown within dotted line 262, each second sensor point opening configured to overlap a part of the fourth electrode 230 and/or a part of the fifth electrode 232 of the electrode assembly. The secondary sensor point openings 262 comprise, in the illustrated exemplary first adhesive layer, five secondary first sensor point openings 262A each configured to overlap a part of the fifth electrode 232. The secondary sensor point openings 262 comprise, in the illustrated exemplary first adhesive layer, four secondary second sensor point openings 262B each configured to overlap a part of the fourth electrode 230. The sensor point openings of the first adhesive layer comprise tertiary sensor point openings shown within dotted line 264, each tertiary sensor opening configured to overlap a part of the fifth electrode 232 and/or a part of the ground electrode 222 of the electrode assembly. The tertiary sensor point openings 264 comprise, in the illustrated exemplary first adhesive layer, five tertiary first sensor point openings 264A each configured to overlap a part of the fifth electrode 232.

Figure 9:
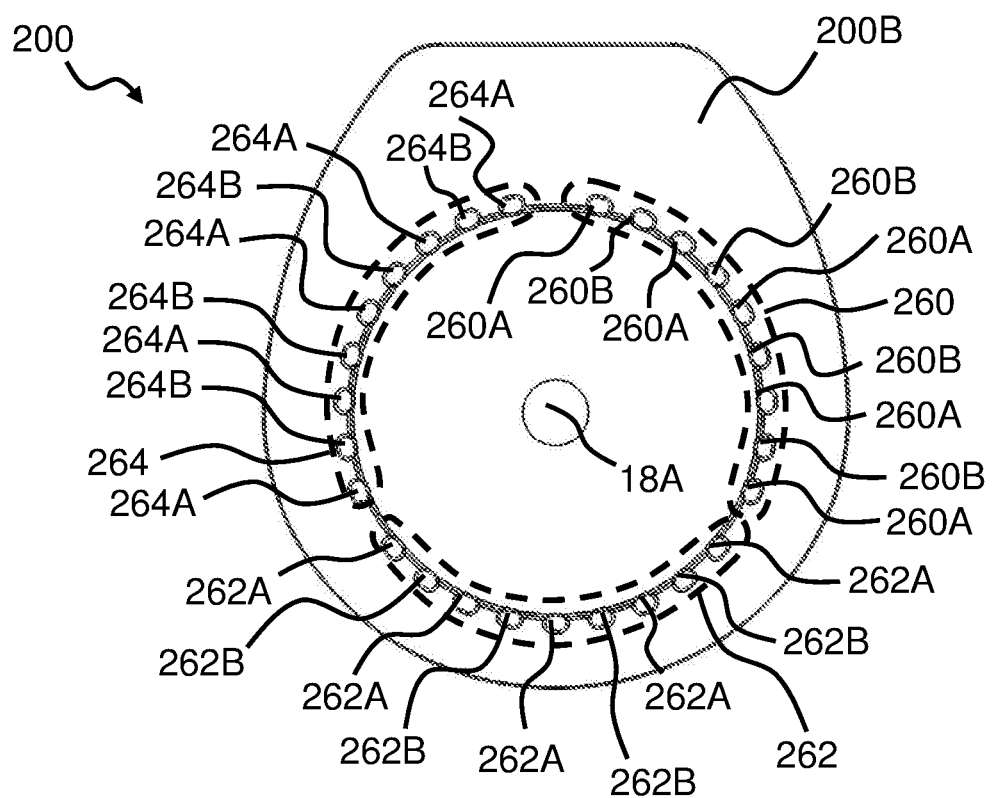
FIG. 9 is a proximal view of the first adhesive layer of FIG. 8.

The tertiary sensor point openings 264 comprise, in the illustrated exemplary first adhesive layer, four tertiary second sensor point openings 264B each configured to overlap a part of the ground electrode 222. FIG. 9 is a proximal view of the first adhesive layer of FIG. 8.

Figure 10:
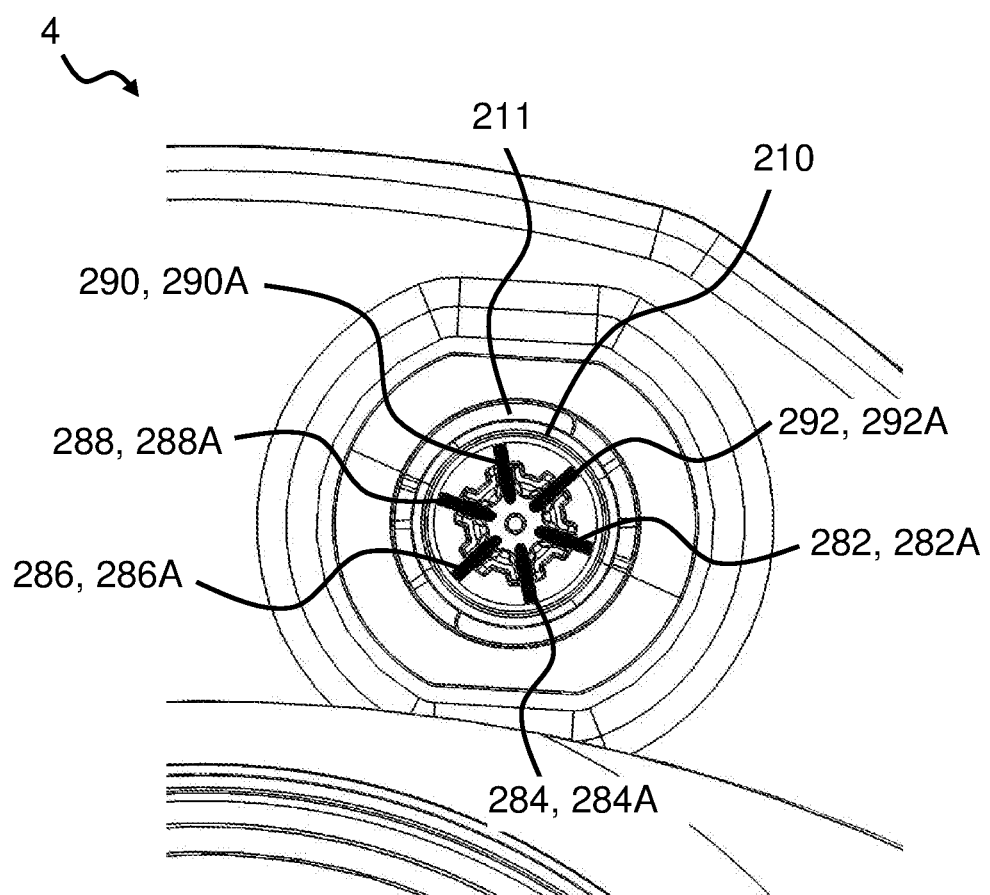
FIG. 10 is a distal view of a part of the base plate including monitor interface.

FIG. 10 is a more detailed distal view of a part of the base plate 4. Monitor interface of the base plate comprises the first connector 211. The first connector 211 comprises coupling part 210 configured to releasably couple the monitor device to the base plate and thus forming a releasable coupling. The first connector 211/monitor interface comprises a plurality of terminals formed by respective terminal elements for forming respective electrical connections with respective terminals of the monitor device.

The plurality of terminals of the first connector 211/ monitor interface comprises a ground terminal element 282 forming a ground terminal 282A, a first terminal element 284 forming a first terminal 284, a second terminal element 286 forming a second terminal 286A, and optionally a third terminal element 288 forming a third terminal 288A. The monitor interface optionally comprises a fourth terminal element 290 forming a fourth terminal 290A and/or a fifth terminal element 292 forming a fifth terminal 290. The terminal elements 282, 284, 286, 288, 290, 292 contact respective connection parts 222A, 224A, 226A, 228A, 230a, 232A of electrodes 222, 224, 226, 228, 230, 232.

The position of the first connector on the base plate, the number of terminals and the position of the terminals in the coupling part may be adapted to the electrode configuration used in the electrode assembly of the base plate.

Figure 11:
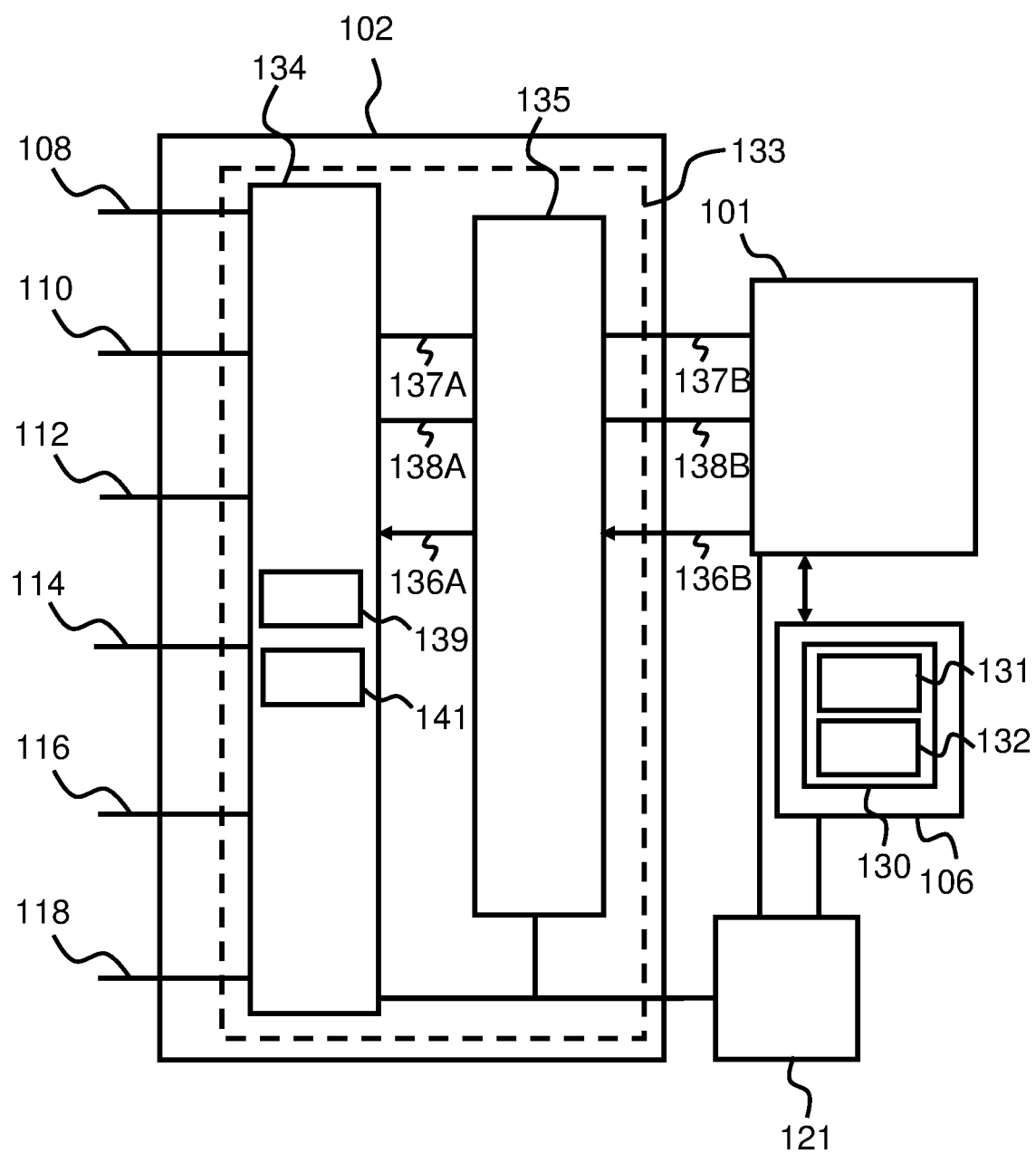
FIG. 11 illustrates the first interface of the exemplary monitor device of the ostomy system.

FIG. 11 illustrates the first interface 102 of the exemplary monitor device 6 of the ostomy system 1. As stated above, the first interface 102 is configured as an appliance interface for electrically connecting the monitor device 6 (illustrated in FIGS. 1 and 2) to the ostomy appliance, e.g., the ostomy appliance 2 (illustrated in FIG. 1). In embodiments, the first interface 102 may electrically connect the ostomy appliance 2 to the processor 101 and/or memory 106 of the monitor device 6.

To electrically connect the monitor device 6 to the ostomy appliance 2, the first interface 102 comprises a ground terminal 108, a first terminal 110, a second terminal 112, a third terminal 114, a fourth terminal 116, and a fifth terminal 118. Each of the terminals 108, 110, 112, 114, 116, 118 connects to a respective electrode of the electrodes 216 (illustrated in FIG. 6). In particular, the ground terminal 108 is configured to connect to the ground electrode 222 (illustrated in FIG. 6) via the ground terminal element 282 (illustrated in FIG. 10), the first terminal 110 is configured to connect to the first electrode 224 (illustrated in FIG. 6) via the first terminal element 284 (illustrated in FIG. 10), the second terminal 112 is configured to connect to the second electrode 226 (illustrated in FIG. 6) via the second terminal element 286 (illustrated in FIG. 10), the third terminal 114 is configured to connect to the third electrode 228 (illustrated in FIG. 6) via the third terminal element 288 (illustrated in FIG. 10), the fourth terminal 116 is configured to connect to the fourth electrode 230 (illustrated in FIG. 6) via the fourth terminal element 290 (illustrated in FIG. 10), and the fifth terminal 118 is configured to connect to the fifth electrode 232 (illustrated in FIG. 6) via the fifth terminal element 292 (illustrated in FIG. 10). Because of these connections, the terminals 108, 110, 112, 114, 116, 118 can respectively receive signals from the ground electrode 222, the first electrode 224, the second electrode 226, the third electrode 228, the fourth electrode 230, and the fifth electrode 232. While the first interface 102 depicts a ground terminal 108, a first terminal 110, a second terminal 112, a third terminal 114, a fourth terminal 116, and a fifth terminal 118, the first interface 102 may include fewer or more terminals in alternative embodiments. For example, the first interface 102 may only include a ground terminal 108 and a first terminal 110.

As set forth above, the electrodes 222, 224, 226, 228, 230, 232 may have different arrangements on the base plate 4 (illustrated in FIG. 1) of the ostomy appliance 2 and/or perform different functions. Due to these different arrangements and/or functions, the signals from the electrodes 222, 224, 226, 228, 230, 232 via the terminals 108, 110, 112, 114, 116, 118 may be collected by the first interface 102 and/or stored on the memory 106 according to different data collection schemes 130. For example, the processor 101 may access the memory 106 and instruct the first interface 102 to collect data from the terminals 108, 110, 112, 114, 116, 118 according to a primary data collection scheme 131 and/or a secondary data collection scheme 132. Additionally or alternatively, the data collection schemes 130 may be collected according to different data collections schemes 130 (e.g., the primary data collection scheme 131 or the secondary data collection scheme 132) for other reasons, such as to efficiently allocate the space on the memory 106 and/or based on an operating state of the ostomy appliance 2, as described in more detail below. While the data collection schemes 130 include two data collection schemes (i.e., the primary data collection scheme 131 and the secondary data collection scheme 132) in other embodiments, the data collection schemes 130 includes more than two data collection schemes.

To collect the data, the first interface 102 includes a data collector 133. The data collector 133 may comprise a data collection unit 134 and a data collection controller 135.

The data collection controller 135 controls the data collection unit 134. In particular, the data collection controller 135 may send one or more control signals, via a first control pin 136A, to the data collection unit 134 to collect data according to different data collection schemes 130 (e.g., the primary data collection scheme 131 or the secondary data collection scheme 132). The data collected by the data collection unit 134 may be transmitted from the data collection unit 134 to the data collection controller 135 via first primary and secondary data pins 137A, 138A.

In embodiments, the control signal(s) sent to the data collection unit 134 may be in response to one or more control signals from the processor 101. In particular, the processor 101 may send one or more control signals, via a second control pin 136B, to the data collection controller 135 and, in response, the data collection controller 135 may send one or more control signals, via the first control pin 136A, to the data collection unit 134. In one or more exemplary monitor devices 5, the data collection controller 135 is connected to the memory 106 and stores the collected data (ostomy data) directly in the memory 106. In addition, the data transmitted from the data collection unit 134 to the data collection controller 135 via the first primary and secondary data pins 137A, 138A may be transmitted from the data collection controller 135 to the processor 101 via the second primary and secondary data pins 137B, 138B. The processor 101 may then store the data collected in memory 106.

The data collector unit 134 may include one or more analog-to-digital converters (ADC) 139. The ADC 139 may receive signals via the terminals 108, 110, 112, 114, 116, 118 and convert the signals from the analog domain (e.g., voltage) to the digital domain (e.g., digital signal). In embodiments, the signal acquisition range of the ADC 139 may be controlled by a control signal sent from the data collection controller 135 to the data collection unit 134 via the first control pin 136A. The signal acquisition range of the ADC 139 may be adapted in response to one or more control signals to optimize a signal-to-noise ratio of any signals received via the terminals 108, 110, 112, 114, 116, 118. Additionally or alternatively, the ADC 139 may be adapted in response to which of the terminals 108, 110, 112, 114, 116, 118 data are being collected. For example, the ADC 139 may be adapted in response to which of the first, second, and/or third resistive pairs 224B, 226B, 228B data is being collected.

Additionally or alternatively, the data collector unit 134 may include one or more multiplexers 141. In embodiments, the signals received from the terminals 108, 110, 112, 114, 116, 118 may be multiplexed by the multiplexer 141 and transmitted to the data collection controller 135. That is, the data collection controller 135 may send a signal to the multiplexer 141 via the first control pin 136A in response to receiving a control signal from the processor 101 via the second control pin 136B that indicates from which of the terminals 108, 110, 112, 114, 116, 118 data are to be collected. For example, the primary data collection 131 scheme may be used for collecting data via a first set of terminals of the terminals 108, 110, 112, 114, 116, 118 and the secondary data collection scheme 132 may be used for collecting data via a second set of terminals of the terminals 108, 110, 112, 114, 116, 118 such that the first set of terminals is different from the second set of terminals. For example, the first set of terminals may comprise the terminals 108, 110, 112, 114 and the second set of terminals may comprise the terminals 108, 116, 118. Due to the first set of terminals comprising the terminals 108, 110, 112, 114, the primary data collection scheme 138 may be used to collect data of the first resistive pair 224B, the second resistive pair 226B, and the third resistive pair 228B. Further, due to the second set of terminals comprising the terminals 108, 116, 118, the secondary data collection scheme 132 may be used to collect data of the sensor parts 222B, 228B, 230B. While the first set of terminals is described as including 108, 110, 112, 114 and the second set of terminals is described as including the terminals 108, 116, 118 this is only an example and not meant to be limiting. After the multiplexer 141 receives data from one or more of the terminals 108, 110, 112, 114, 116, 118, the data may be transmitted to the data collection controller 135 via the first primary and secondary data pins 137A, 138A.

In embodiments, the primary data collection scheme 131 may differ from the secondary data collection scheme 132 by their respective sampling rates. For example, the data collection unit 134 may sample the resistance between the first resistive pair 224B, the second resistive pair 226B, the third resistive pair 228B, and/or between two sensor points via one or more of the terminals 108, 110, 112, 114, 116, 118 and the sampling rate of the samples may be different depending on whether the primary data collection scheme 131 is implemented or the secondary data collection scheme 132 is implemented. That is, the sampling rate of the primary data collection scheme 131 may be at a first sampling rate and the sampling rate of the secondary collection scheme 132 may be at a second sampling rate such that the first sampling rate is different than the second sampling rate. For example, the primary data collection scheme 131 may include a sampling rate between 0.01 Hz to 0.5 kHz and the secondary data collection scheme 132 may comprise a sampling rate between 0.1 Hz to 1.0 kHz.

Additionally or alternatively, the primary data collection scheme 131 may differ from the secondary data collection scheme 132 by their respective number of samples per measurement. That is, each measurement saved to memory 106 may be comprised of a number of samples (e.g., the sampled resistance between the first resistive pair 224B, the second resistive pair 226B, the third resistive pair 228B, and/or between two sensor points). And, the number of samples per measurement may differ depending on whether the primary data collection scheme 131 is implemented or the secondary data collection scheme 132 is implemented. That is, a measurement of the primary data collection scheme 131 may include a first number of samples and a measurement of the secondary data collection scheme 132 may include a second number of samples such that the first number of samples is different than the second number of samples. For example, the primary data collection scheme 131 may comprise ten (10) samples to a measurement and the secondary data collection scheme 132 may comprise one hundred (100) samples to a measurement.

Additionally or alternatively, the primary data collection scheme 131 may differ from the secondary data collection scheme 132 by their respective measurement rates. In particular, each measurement may be comprised of one or more samples (e.g., the sampled resistance between the first resistive pair 224B, the second resistive pair 226B, the third resistive pair 228B, and/or between two sensor points). And, the measurement rates may differ depending on whether the primary data collection scheme 131 is implemented or the secondary data collection scheme 132 is implemented. That is, the measurement rate of the primary data collection scheme 131 may be at a first measurement rate and the measurement rate of the secondary collection scheme 132 may be at a second measurement rate such that the first measurement rate is different than the second measurement rate. For example, the primary data collection scheme 131 may include a measurement rate at 1-10 minutes and/or the secondary data collection scheme 132 may comprise a measurement rate at 1-5 minutes.

As stated above, different data collection schemes 130 (e.g., the primary data collection scheme 131 and/or the secondary data collection scheme 132) may implemented based on an operating state of the ostomy appliance 2. Embodiments of the operating state of the ostomy appliance 2 include but are not limited to the following examples.

In embodiments, different data collection schemes 130 (e.g., the primary data collection scheme 131 and/or the secondary data collection scheme 132) may be implemented based on the orientation of the user. For example, if the user is standing up, a data collection scheme 130 (e.g., the primary data collection scheme 131) may be implemented that is different than the data collection scheme 130 (e.g., the secondary data collection scheme 132) that is implemented when the user is lying down. The reason being is because the adhesion between the first adhesive layer 200 and the skin surface of the user will likely degrade at a faster rate due to movement and, perhaps, increased perspiration when the user is standing up. As such, a data collection scheme 130 that collects data at, for example, a greater sampling rate, a greater measurement rate, and/or a greater number of samples per measurement, may be implemented when the user is standing up versus the data collection scheme 130 that is implemented when the user is lying down to, perhaps, save power consumed by the data collector 133 and/or better utilize the storage capacity of the memory 106. In embodiments, the orientation of the user may be determined by the sensor unit 140.

In embodiments, different data collection schemes 130 (e.g., the primary data collection scheme 131 and/or the secondary data collection scheme 132) may be implemented based on the activity level of the user. For example, if the user's activity level is high a data collection scheme 130 (e.g., the primary data collection scheme 131) may be implemented that is different than the data collection scheme 130 (e.g., the secondary data collection scheme 132) that is implemented when the user is being less active. The reason being is because the adhesion between the first adhesive layer 200 and the skin surface of the user will likely degrade at a faster rate due to movement and, perhaps, increased perspiration when the user's activity level is high. As such, a data collection scheme 130 that collects data at, for example, a greater sampling rate, a greater measurement rate, and/or a greater number of samples per measurement, may be implemented when the activity level is high versus the data collection scheme 130 that is implemented when the activity level is low to, perhaps, save power consumed by the data collector 133 and/or better utilize the storage capacity of the memory 106. In embodiments, the activity level of the user may be determined by the sensor unit 140.

In embodiments, different data collection schemes 130 (e.g., the primary data collection scheme 131 and/or the secondary data collection scheme 132) may be implemented based on a separation between the monitor device 6 and an accessory device 8. For example, if signals (e.g., Bluetooth signals) of the monitor device 6 are out of range of signals (e.g., Bluetooth signals) of the accessory device 8, a data collection scheme 130 (e.g., the primary data collection scheme 131) may be implemented that is different than a data collection scheme 130 (e.g., the secondary data collection scheme 132) that is implemented when signals of the monitor device 6 are within range of signals of the accessory device 8. The reason being is because, in embodiments, the accessory device 8 may provide notifications to the user of the adhesion between the first adhesive layer 200 and the skin surface of the user and/or whether output is leaking between the first adhesive layer 200 and the skin surface of the user. If the user is unable to receive these notifications, then a data collection scheme 130 that collects data at, for example, a lower sampling rate, a lower measurement rate, and/or a lower number of samples per measurement, may be implemented when the signals of the monitor device 6 are out of range of signals of the accessory device 8 versus the data collection scheme 130 that is implemented when the signals of the monitor device 6 are within range of signals of the accessory device 8 to, perhaps, save power consumed by the data collector 133 and/or better utilize the storage capacity of the memory 106. In embodiments, the separation between the monitor device 6 and the accessory device 8 may be determined by the second interface 104.

In embodiments, different data collection schemes 130 (e.g., the primary data collection scheme 131 and/or the secondary data collection scheme 132) may be implemented based on the power capacity of the power unit 121. For example, if the power capacity of the power unit 121 is below a threshold then a data collection scheme 130 (e.g., the primary data collection scheme 131) may be implemented that is different than the data collection scheme 130 (e.g., the secondary data collection scheme 132) that is implemented when the power capacity of the power unit 121 is above a threshold. The reason being is because, in embodiments, the power unit 121 may be more likely to run out of power and, therefore, be unable to provide indications of the quality of adhesion between the first adhesive layer 200 and the skin surface of the user and/or whether output is leaking between the first adhesive layer 200 and the skin surface of the user. As such, a data collection scheme 130 that collects data at, for example, a lower sampling rate, a lower measurement rate, and/or a lower number of samples per measurement, may be implemented when the power capacity of the power unit 121 is below a threshold versus the data collection scheme 130 that is implemented when the power capacity of the power unit 121 is above a threshold to, perhaps, save power of the power unit 121. In embodiments, the power capacity of the power unit 121 may be determined by the processor 101.

In embodiments, different data collection schemes 130 (e.g., the primary data collection scheme 131 and/or the secondary data collection scheme 132) may be implemented based on the model type of the ostomy appliance 2. For example, some models of an ostomy appliance 2 may have better or worse adhesion between the first adhesive layer 200 and the skin surface of the user. As such, a data collection scheme 130 that collects data at, for example, a higher sampling rate, a higher measurement rate, and/or a higher number of samples per measurement, may be implemented when the ostomy appliance 2 is a first model type having worst adhesion versus the data collection scheme 130 that is implemented when the ostomy appliance 2 is a second model type having better adhesion to, perhaps, allow timely detection of a leak. In embodiments, the model type of the ostomy appliance 2 may be input into the processor 101, sensed by the sensor unit 140, and/or the like.

In embodiments, different data collection schemes 130 (e.g., the primary data collection scheme 131 and/or the secondary data collection scheme 132) may be implemented be based on the wear time of the ostomy appliance 2. For example, a data collection scheme 130 that collects data at, for example, a higher sampling rate, a higher measurement rate, and/or a higher number of samples per measurement, may be implemented when the user has been wearing the ostomy appliance 2 for a period of time that exceeds a threshold versus the data collection scheme 130 that is implemented when the user has been wearing the ostomy appliance 2 for a period of time that doesn't exceed the threshold. An advantage of collecting data at a higher sampling rate, a higher measurement rate, and/or a higher number of samples per measurement when the wear time is greater than a threshold is because the adhesion between the first adhesive layer 200 and the skin surface of the user will likely degrade over time and, therefore, the likelihood of a leak increases. In embodiments, the processor 101 may determine whether the wear time has surpassed the threshold. Additionally or alternatively, the threshold may be input into the monitor device 6 and/or based on a previous wear time of the ostomy appliance 2 by the user.

In embodiments, different data collection schemes 130 (e.g., the primary data collection scheme 131 and/or the secondary data collection scheme 132) may be implemented based on a user's preferences. For example, when the user has a preference that he/she would like to know within a threshold period of time that the adhesion between the first adhesive layer 200 and the skin surface of the user degrades below a threshold amount, a specific data collection 130 scheme may be implemented to allow the user to be notified within said threshold period. Basing the data collection scheme 130 on a user's preference may provide piece of mind for the user.

In embodiments, different data collection schemes 130 (e.g., the primary data collection scheme 131 and/or the secondary data collection scheme 132) may be implemented based on the location of the user. For example, users of ostomy appliances 2 may differ in their ostomy habits based on the location of the users. For example, users in a first country may change their ostomy appliances 2 more frequently than users in a second country due to, perhaps, better healthcare subsidies. As such, users in the first country may wish to have quicker notifications of adhesion degradation than users in the second country. Accordingly, a data collection scheme 130 that collects data at, for example, a higher sampling rate, a higher measurement rate, and/or a higher number of samples per measurement, may be implemented when the ostomy appliance 2 is being used in a first location versus the data collection scheme 130 that is implemented when the ostomy appliance 2 is being used in a second location to, perhaps, allow quicker notifications about adhesion degradation.

In embodiments, different data collection schemes 130 (e.g., the primary data collection scheme 131 and/or the secondary data collection scheme 132) may be implemented based on if a user cuts, for example, a resistive pair (e.g., the first, second, and/or third resistive pairs 224B, 226B, 228B) when configuring the stomal opening 18. For example, a data collection scheme 130 that collects data at, for example, a lower sampling rate, a lower measurement rate, and/or a lower number of samples per measurement, may be implemented for a cut resistive pair versus a data collection scheme 130 that is implemented on a non-cut resistive pair to, perhaps, save power consumed by the data collector 133 and/or better utilize the storage capacity of the memory 106.

In embodiments, different data collection schemes 130 (e.g., the primary data collection scheme 131 and/or the secondary data collection scheme 132) may be implemented based on the wetting of a resistive pair (e.g., the first, second, and/or third resistive pairs 224B, 226B, 228B). For example, a data collection scheme 130 that collects data at, for example, a lower sampling rate, a lower measurement rate, and/or a lower number of samples per measurement may be implemented for a wet resistive pair versus a data collection scheme 130 that is implemented on a non-wet resistive pair to, perhaps, save power consumed by the data collector 133 and/or better utilize the storage capacity of the memory 106.

Figure 12:
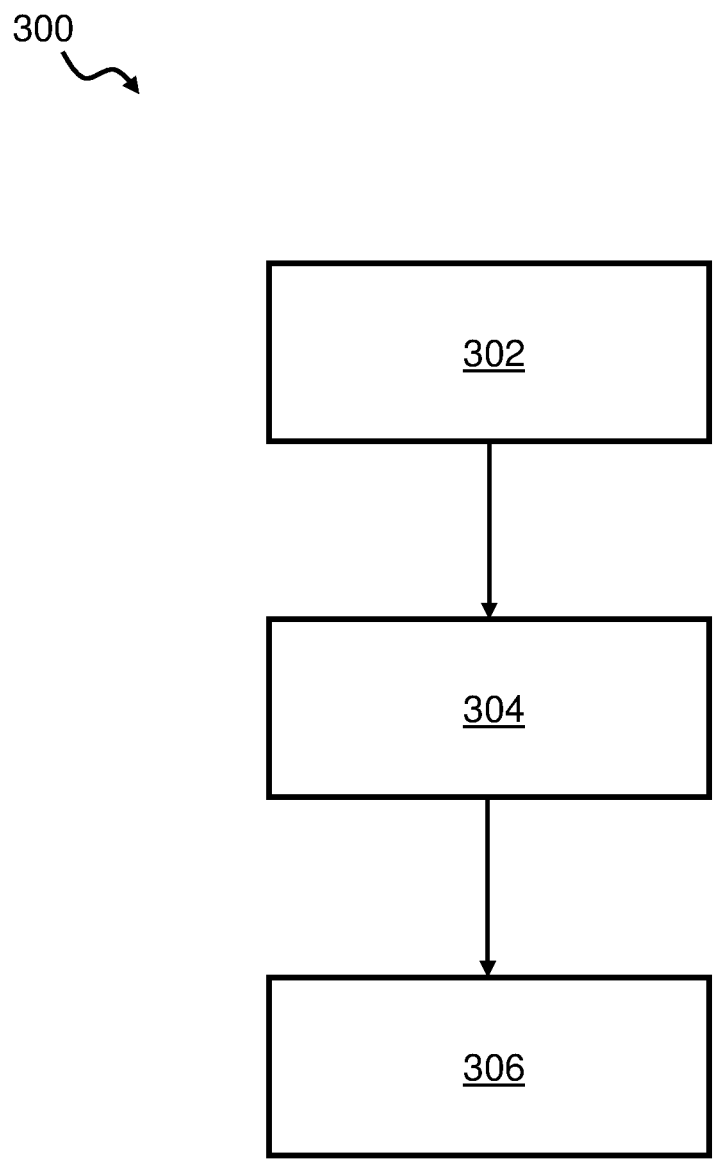
FIG. 12 illustrates a flow diagram of a method for data collection from an ostomy appliance.
Figure 13:
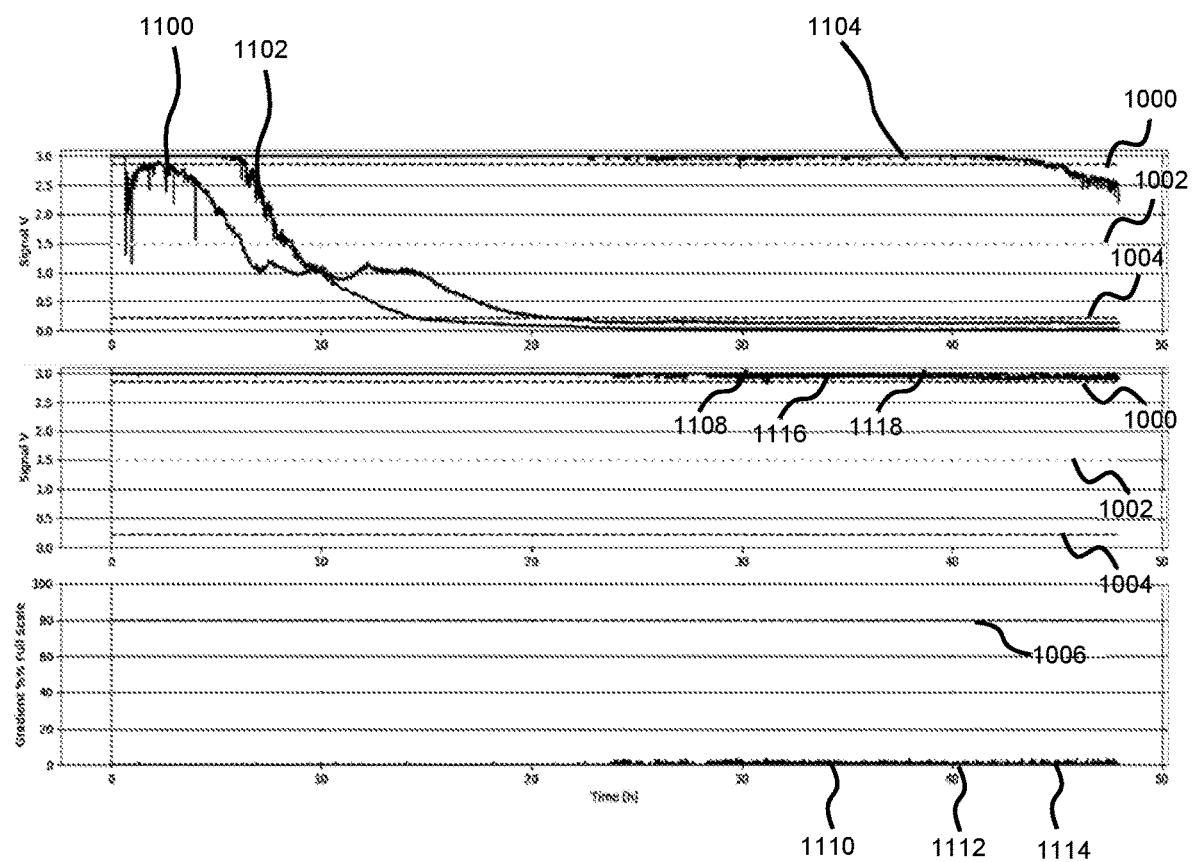
FIG. 13 is an exemplary graphical representation of parameter data as a function of time.

FIG. 12 illustrates a flow diagram of a method 300 for data collection from an ostomy appliance. To facilitate describing method 300, reference is made to the other figures, in particular, FIGS. 1, 2, 6, and 11.

In embodiments, the method 300 comprises collecting data from a first terminal and a second terminal according to a primary data collection scheme 131 (block 302). In embodiments, the data may be collected by the data collector 133 and the first terminal and the second terminal may be one or more of the terminals 108, 110, 112, 114, 116, 118. Because of these connections, the terminals 108, 110, 112, 114, 116, 118 can respectively receive signals from the ground electrode 222, the first electrode 224, the second electrode 226, the third electrode 228, the fourth electrode 230, and the fifth electrode 232.

The method 300 further comprises collecting data from the first terminal and the second terminal according to a secondary data collection scheme 132 (block 304). In embodiments, the primary data collection scheme 131 is different from the secondary data collection scheme 132. For example, the sampling frequency of the primary data collection scheme 131 may be different than the sampling frequency of the secondary data collection scheme 132. Additionally or alternatively, the number of samples per measurement of the primary data collection scheme 131 may be different than the number of samples of the secondary data collection scheme 132. Additionally or alternatively, the measurement frequency of the primary data collection scheme 131 may be different than the measurement frequency of the secondary data collection scheme 132.

In embodiments, the method 300 further comprises selecting the data collection scheme 130 in accordance with an operating state of the ostomy appliance 2 (block 306). In embodiments, the operating state of the ostomy appliance 2 may be sent by the processor 101 to the data collector 133 via a control signal. Examples of the operating state of the ostomy appliance 2 include, but are not limited to, the orientation of the user, the activity level of the user, whether signals of the monitor device 102 are within signals of the accessory device 8, the power capacity of the power unit 121, the model type of the ostomy appliance 2, the wear time of the ostomy appliance 2, user preferences, and/or a location of the user of the ostomy appliance 2.

The position of the first connector on the base plate, the number of terminals and the position of the terminals in the coupling part may be adapted to the electrode configuration used in the electrode assembly of the base plate.

Figure 14:
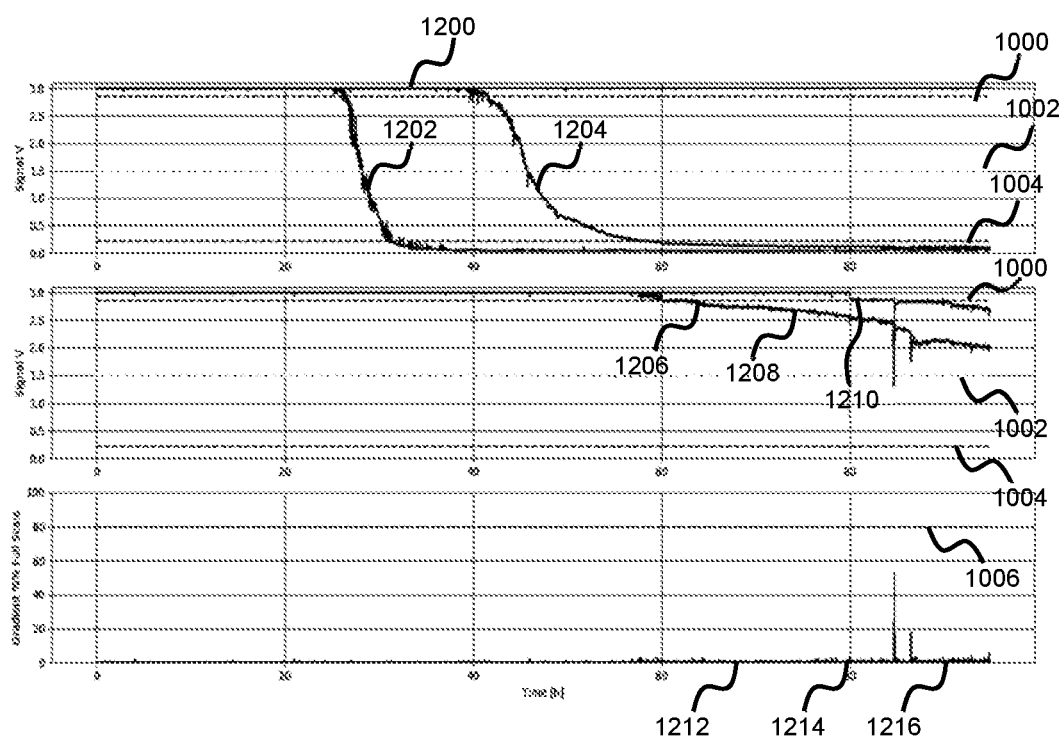
FIG. 14 is an exemplary graphical representation of parameter data as a function of time.

FIG. 14 shows an exemplary graphical representation of parameter data as a function of time. In this example, the parameter data in the y-axis is in Volts and time is in the x-axis. Curve 1100 shows, as a function of time, a first parameter data indicative of voltage measured by the first electrode pair of the base plate. Curve 1102 shows, as a function of time, a second parameter data indicative of voltage measured by the second electrode pair of the base plate. Curve 1104 shows, as a function of time, a third parameter data indicative of voltage measured by the third electrode pair of the base plate. Curves 1108, 1116, 1118 show, as a function of time, fourth primary parameter indicative of voltage measured by the fourth electrode pair of the base plate, fourth secondary parameter indicative of voltage measured by the fourth electrode and the fifth electrode of the base plate, and fourth tertiary parameter indicative of voltage measured by the fifth electrode pair of the base plate respectively. Curves 1110, 1112, 1114 show, as a function of time, a gradient of fourth primary parameter indicative of voltage gradient measured by the fourth electrode pair of the base plate, a gradient of fourth secondary parameter indicative of voltage gradient measured by the fourth electrode and the fifth electrode of the base plate, and a gradient of fourth tertiary parameter indicative of voltage gradient measured by the fifth electrode pair of the base plate respectively. FIG. 14 shows the upper voltage threshold value represented as curve 1000, the medium voltage threshold value represented as curve 1002, the lower voltage threshold value represented as curve 1004, and curve 1006 is a gradient limit.

Curves 1108, 1116, 1118 as well as curves 1110, 1112, 1114 show that no moisture is detected at the proximal side of the first adhesive layer by the fourth electrode pair.

At a time less than 5 h, curve 1100 shows that moisture is detected by the first electrode pair as the first parameter data crosses the upper voltage threshold value while curve 1102 shows that moisture is not detected by the second electrode pair as the second parameter data has not crossed the upper voltage threshold value. At this stage, it is determined that the ostomy appliance is in a first operating state.

At time between 5 h and 10 h, curve 1102 shows that moisture is detected by the second electrode pair as the second parameter data crosses the upper voltage threshold value. At this stage, it is determined that the ostomy appliance is in a second operating state.

At time around 45 h, curve 1104 shows that moisture is detected by the third electrode pair as the third parameter data crosses the upper voltage threshold value. At this stage, it is determined that the ostomy appliance is in a third operating state.

Figure 15:
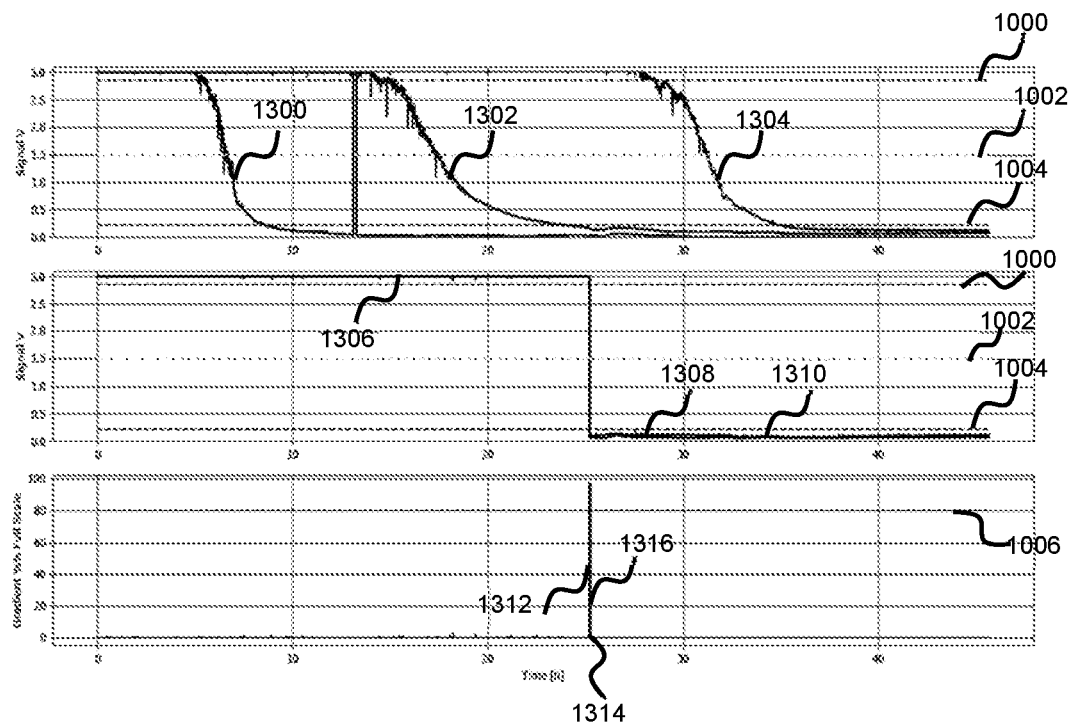
FIG. 15 is an exemplary graphical representation of parameter data as a function of time.

FIG. 15 shows an exemplary graphical representation of parameter data as a function of time. In this example, the parameter data in the y-axis is in Volts and time is in the x-axis.

Curve 1202 shows, as a function of time, a first parameter data indicative of voltage measured by the first electrode pair of the base plate. Curve 1204 shows, as a function of time, a second parameter data indicative of voltage measured by the second electrode pair of the base plate. Curve 1200 shows, as a function of time, a third parameter data indicative of voltage measured by the third electrode pair of the base plate. Curves 1206, 1208, 1210 show, as a function of time, fourth primary parameter indicative of voltage measured by the fourth electrode pair of the base plate, fourth secondary parameter indicative of voltage measured by the fourth electrode and the fifth electrode of the base plate, and fourth tertiary parameter indicative of voltage measured by the fifth electrode pair of the base plate respectively. Curves 1212, 1214, 1216 show, as a function of time, a gradient of fourth primary parameter indicative of voltage gradient measured by the fourth electrode pair of the base plate, a gradient of fourth secondary parameter indicative of voltage gradient measured by the fourth electrode and the fifth electrode of the base plate, and a gradient of fourth tertiary parameter indicative of voltage gradient measured by the fifth electrode pair of the base plate respectively. FIG. 26 shows the upper voltage threshold value represented as curve 1000, the medium voltage threshold value represented as curve 1002, the lower voltage threshold value represented as curve 1004, and curve 1006 represents a gradient limit.

Curves 1206, 1208, 1210 as well as curves 1212, 1214, 1216 show that moisture is detected at the proximal side of the first adhesive layer by the fourth electrode pair, the fourth and fifth electrode, and the fifth electrode pair at a time starting at 60 h until 90 h. As the three electrode pairs are triggered as shown by the decreases shown by 1206, 1208, 1210 and as the curves 1212, 1214, 1216 show a gradient below 80%, this is indicative of the presence of sweat at the proximal side of the first adhesive layer.

At a time of 30 min, curve 1202 shows that moisture is detected by the first electrode pair as the first parameter data crosses the upper voltage threshold value while curve 1204 shows that moisture is not detected by the second electrode pair as the second parameter data has not crossed the upper voltage threshold value. At this stage, it is determined that the ostomy appliance is in a first operating state.

At time around 40 h, curve 1204 shows that moisture is detected by the second electrode pair as the second parameter data crosses the upper voltage threshold value. At this stage, it is determined that the ostomy appliance is in a second operating state.

Figure 16:
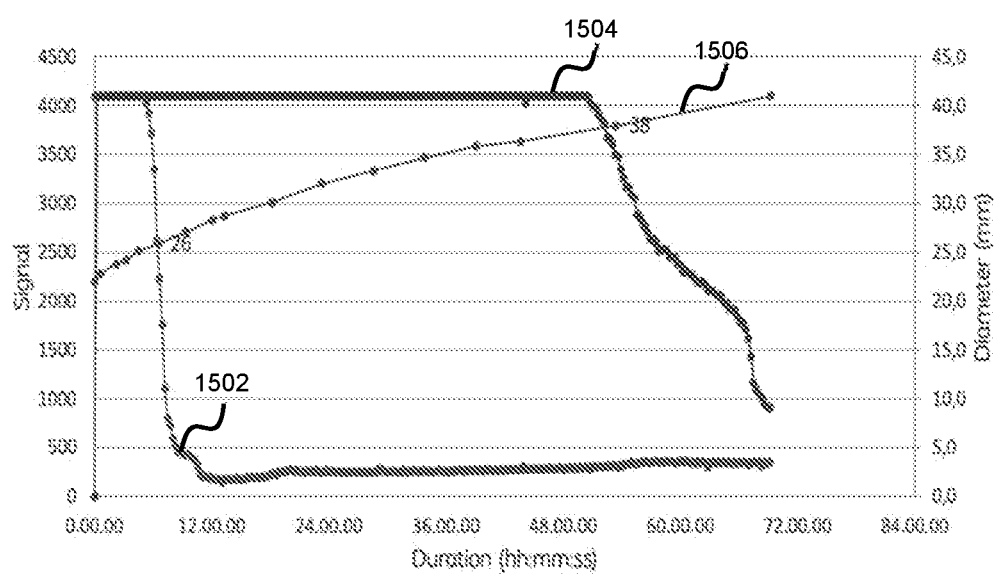
FIG. 16 is an exemplary graphical representation of parameter data as a function of time and a whitening zone diameter as a function of time.

FIG. 16 shows an exemplary graphical representation of parameter data as a function of time. In this example, the parameter data in the y-axis is in Volts and time is in the x-axis. Curve 1300 shows, as a function of time, a first parameter data indicative of voltage measured by the first electrode pair of the base plate. Curve 1302 shows, as a function of time, a second parameter data indicative of voltage measured by the second electrode pair of the base plate. Curve 1304 shows, as a function of time, a third parameter data indicative of voltage measured by the third electrode pair of the base plate. Curves 1306, 1308, 1310 show, as a function of time, fourth primary parameter indicative of voltage measured by the fourth electrode pair of the base plate, fourth secondary parameter indicative of voltage measured by the fourth electrode and the fifth electrode of the base plate, and fourth tertiary parameter indicative of voltage measured by the fifth electrode pair of the base plate respectively. Curves 1312, 1314, 1316 show, as a function of time, a gradient of fourth primary parameter indicative of voltage gradient measured by the fourth electrode pair of the base plate, a gradient of fourth secondary parameter indicative of voltage gradient measured by the fourth electrode and the fifth electrode of the base plate, and a gradient of fourth tertiary parameter indicative of voltage gradient measured by the fifth electrode pair of the base plate respectively. FIG. 16 shows the upper voltage threshold value represented as curve 1000, the medium voltage threshold value represented as curve 1002, the lower voltage threshold value represented as curve 1004, and curve 1006 is a gradient limit.

Curves 1306, 1308, 1310 as well as curves 1312, 1314, 1316 show that moisture is detected at the proximal side of the first adhesive layer by the fourth electrode pair at a time starting at around 25 h. As leakage electrodes (i.e. the fourth electrode pair, the fourth and fifth electrode, and the fifth electrode pair) are trigger as shown by the decreases shown by 1306, 1308, 1310 and as curve 1312, 1314, 1316 show a gradient above 80%, this is indicative of the presence of output at the proximal side of the first adhesive layer. This indicate severe leakage. It may be determined that the ostomy appliance is in a sixth operating state.

At a time of 5 h, curve 1300 shows that moisture is detected by the first electrode pair as the first parameter data crosses the upper voltage threshold value while curve 1302 shows that moisture is not detected by the second electrode pair as the second parameter data has not crossed the upper voltage threshold value. At this stage, it is determined that the ostomy appliance is in a first operating state.

At time around 15 h, curve 1302 shows that moisture is detected by the second electrode pair as the second parameter data crosses the upper voltage threshold value. At this stage, it is determined that the ostomy appliance is in a second operating state.

At time around 30 h, curve 1304 shows that moisture is detected by the third electrode pair as the third parameter data crosses the upper voltage threshold value. In an example where the curves 1306, 1308, 1310 had not dropped below corresponding thresholds, curve 1304 indicates that moisture has reached the third electrode pair, and the present disclosure enables determining that the ostomy appliance is in a third operating state.

Figure 17A:
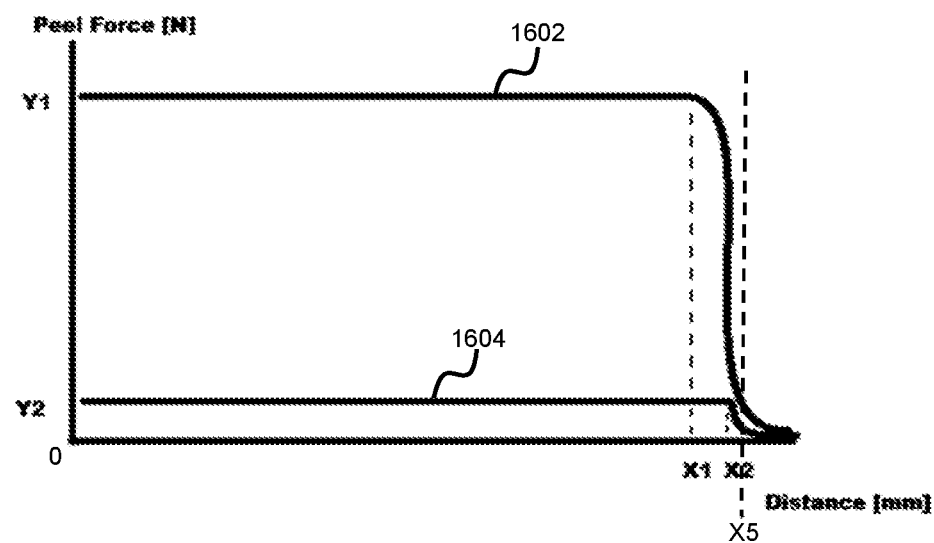
FIGS. 17A-17B are exemplary graphical representations of peel force as a function of a peeling distance travelled by a peeling action exercising the peel force on a first adhesive layer of a base plate.
Figure 17B:
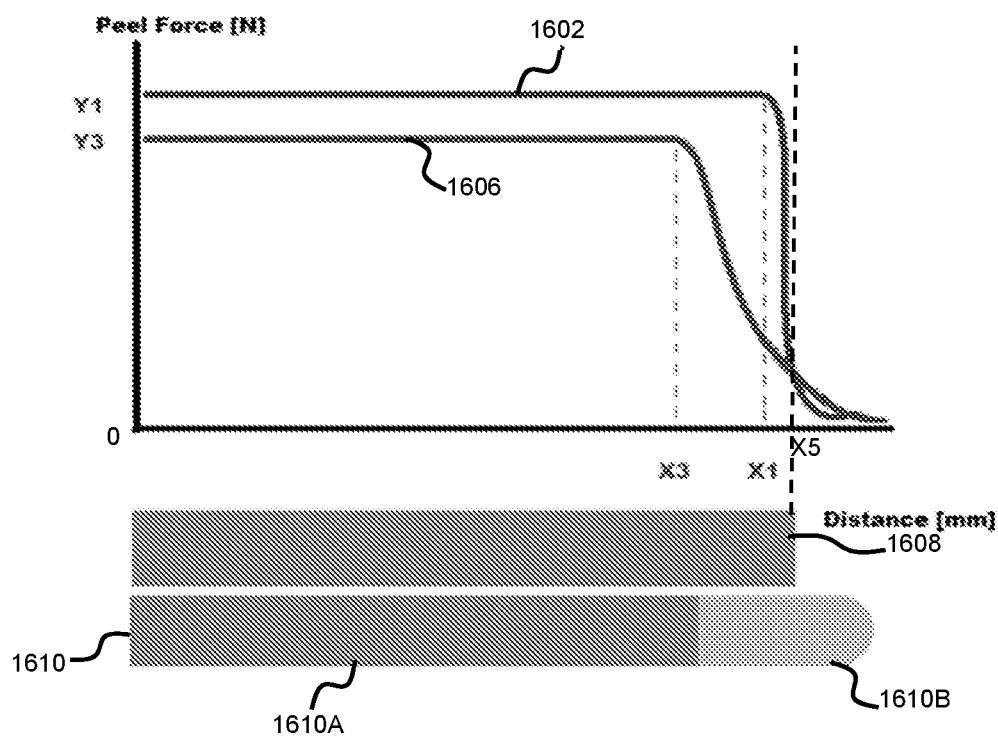

FIG. 17 shows an exemplary graphical representation of parameter data as a function of time and a whitening zone diameter (e.g. related to a radial thickness of a whitening ring surrounding the stomal opening) as a function of time. FIG. 17 illustrates the moisture propagation in the first adhesive layer as a function of time and illustrates a correlation between parameter data detected by the first electrode pair and the second electrode pair of the base plate and actual moisture on the proximal surface of the first adhesive layer of the base plate. The actual moisture propagation in the first adhesive layer may appear as a whitening zone (e.g. a white ring around the stomal opening) in the first adhesive layer. Moisture affects the first adhesive layer in that the moisture reacts with the composition of the first adhesive layer to form the white ring around the stomal opening, and thereby reduces adhesive performance of the base plate. FIG. 17 is obtained by experiments where water is applied from the stomal opening of the based plate to follow, using the electrodes of the base plate, the radial propagation of moisture leading to radial erosion of the first adhesive layer of the base plate.

Curve 1502 shows, as a function of time, a first parameter data indicative of voltage measured by the first electrode pair of the base plate. Curve 1504 shows, as a function of time, a second parameter data indicative of voltage measured by the second electrode pair of the base plate. Curve 1506 shows a diameter of the white ring as a function of time. The first parameter data shows a decrease in e.g. voltage measured by the first electrode pair over time. It is also seen that the voltage of the second electrode pair drops at a later time than when the first parameter data shows a decrease in e.g. voltage dropped. This correlates well with the diameter of the white ring which goes from around 25-26 mm when the first electrode pair is triggered (e.g. first parameter data shows a decrease) to 38 mm when the second electrode pair is triggered (second parameter data shows a decrease). This corresponds substantially to the location of the first electrode pair at twice the first radial distance R1, and of the second electrode pair at twice the second radial distance R2.

It is noted that various regions and countries have various routines and recommendations to support optimal use of an ostomy appliance. For example, in regions of Europe, it may be indicated to the user that an ostomy appliance with a base plate as disclosed herein is an optimal state (corresponding to a first operating state) when the radial thickness of the whitening ring is between 0-15 mm (for a user not in compliance with a preferred use), such as between 0-7 mm (for a user in compliance with a preferred use), such as between 0-5 mm (recommended by a nurse).

For example, in Europe, it may be indicated to the user that an ostomy appliance with a base plate as disclosed herein is in suboptimal state (corresponding to a second operating state) and thereby indicate a consideration to change the base plate when the radial thickness of the whitening ring is such as between 5-10 mm (recommended by a nurse), between 7 mm and 10 mm (for a user in compliance with a preferred use), and/or between 15 mm and 30 mm (for a user not in compliance with a preferred use).

For example, in Europe, it may be indicated to the user that an ostomy appliance with a base plate as disclosed herein is in a poor state (corresponding to a third operating state) and indicate a request to change the base plate when the radial thickness of the whitening ring is more than 10 mm (recommended by a nurse), such as more than 15 mm (for a user in compliance with a preferred use), such as more than 30 mm (for a user not in compliance with a preferred use).

For example, in other regions (e.g. America), it may be indicated to the user that an ostomy appliance with a base plate as disclosed herein is an optimal state (corresponding to a first operating state) when the radial thickness of the whitening ring is between 0-20 mm (for a user not in compliance with a preferred use), such as between 0-10 mm (for a user in compliance with a preferred use), such as between 0-10 mm (recommended by a nurse).

For example, in other regions (e.g. America), it may be indicated to the user that an ostomy appliance with a base plate as disclosed herein is in suboptimal state (corresponding to a second operating state) and thereby indicate a consideration to change the base plate when the radial thickness of the whitening ring is such as between 10 mm and 20 mm (recommended by a nurse), between 10 mm and 20 (for a user in compliance with a preferred use), and/or between 20 mm and 40 mm (for a user not in compliance with a preferred use).

For example, in other regions (e.g. America), it may be indicated to the user that an ostomy appliance with a base plate as disclosed herein is in a poor state (corresponding to a third operating state) and indicate a request to change the base plate when the radial thickness of the whitening ring is more than 20 mm (recommended by a nurse), such as more than 20 mm (for a user in compliance with a preferred use), such as more than 40 mm (for a user not in compliance with a preferred use).

The disclosed methods, ostomy appliances, monitor devices, and accessory devices allow to accommodate the regional preferences of user in their use of the ostomy appliance to adjust thresholds for the operating states to the regional preference or use.

FIGS. 18A-18B shows exemplary graphical representations of peel force as a function of a peeling distance travelled by a peeling action exercising the peel force (e.g. perpendicularly to the proximal (or distal) surface of the first adhesive layer) on a first adhesive layer of a base plate disclosed herein. The peel force relates to a required force to peel the first adhesive layer off the skin surface. The peeling distance is with respect to one end of the first adhesive layer where the peel force starts to be exercised. The peeling distance relates to the size or length of the first adhesive layer and thereby may relate to a size or length of a portion the first adhesive layer affected by moisture and of a portion of the first adhesive layer not affected by moisture. The peel forces illustrated in FIGS. 18A-18B are representative of adhesive performance of the first adhesive layer of the base plate to the skin surface.

Composition of the first adhesive layer of the base plate as disclosed herein in one or more embodiments is formulated to provide adhesion of the base plate to the skin surface of the user when the base plate is worn and to maintain a dry and healthy skin surface. Avoiding maceration of skin when occluding the skin with an adhesive is done by transporting sweat away from the skin and into the first adhesive layer by means of e.g. hydrocolloid types and adhesive (e.g. hydrocolloid adhesives) forming part of an absorbing element of the first adhesive layer.

For example, when the absorbing element is in contact with moisture, (e.g. water, sweat, urine or feces), the absorbing element absorb the moisture. This reduces the adhesion of the first adhesive layer to the skin.

For example, the first adhesive layer goes from a dry adhesive state with acceptable adhesive performance (e.g. acceptable adhesion and cohesion) in to a wet adhesive state (e.g. reduced or non-adhesion and low cohesion gel).

Curve 1602 of FIGS. 18A and 18B shows a peel force applied to the first adhesive layer as a function of a peeling distance travelled by a peeling action exercising the peel force on the first adhesive layer in a dry adhesive state, (e.g. not affected by moisture). The peel force is expressed in Newtons while the peeling distance is expressed in mm. The length of the first adhesive layer in dry adhesive state is illustrated by X5, corresponding to length of the first adhesive layer 1608 in dry adhesive state.

Curve 1602 shows that the peel force applied to the first adhesive layer in a dry adhesive state is equal to Y1 when the peeling distance is less than X1. At X1, the peeling force drops as the peeling distance increases towards X5 and the end of the first adhesive layer.

Curve 1604 of FIG. 18A shows a peel force applied to the first adhesive layer as a function of a peeling distance travelled by a peeling action exercising the peel force on the first adhesive layer in a wet adhesive state, (e.g. affected by moisture to the point of reaching a completely wet adhesive state, where the first adhesive layer has become a gel).

Curve 1604 shows that when the peeling distance is less than X2, the peel force applied to the first adhesive layer in a wet adhesive state is equal to Y2 which has much lower value than Y1. This shows that the adhesive performance of the first adhesive layer is reduced when the first adhesive layer is in a wet adhesive state. At X2, the peeling force drops as the peeling distance increases until the end of the first adhesive layer. It is noted that X2 is larger than X1, because the first adhesive layer in a wet adhesive state extends in volume, and thus in length due to the gelling of the components of the first adhesive layer.

The peel experiment illustrated in FIG. 18A shows a loss of adhesive performance when the first adhesive is in a wet adhesive state.

Curve 1606 of FIG. 18B shows a peel force applied to the first adhesive layer as a function of a peeling distance travelled by a peeling action exercising the peel force on the first adhesive layer illustrated 1610 which comprises a first portion 1610A in a dry adhesive state and a second portion 1610B in a wet adhesive state, (e.g. affected by moisture to the point of reaching a completely wet adhesive state, where the first adhesive layer has become a gel).

Curve 1606 shows that when the peeling distance is less than X3, the peel force applied to the first adhesive layer in a wet adhesive state is equal to Y3 which has lower value than Y1. This shows that the adhesive performance of the first adhesive layer is reduced when the first adhesive layer comprises a portion in a wet adhesive state. At X3, the peeling force drops as the peeling distance increases until the end of the first adhesive layer. It is noted that X3 corresponds to the length of the portion 1610A in dry adhesive state.

The peel experiment illustrated in FIG. 18B shows a loss of adhesive performance when the first adhesive is partly in a wet adhesive state.

Accordingly, FIG. 18A-18B demonstrate that the operating state determined based on monitor data is indicative of adhesive performance of the base plate.

The use of the terms "first", "second", "third" and "fourth", "primary", "secondary", "tertiary" etc. does not imply any particular order but are included to identify individual elements. Moreover, the use of the terms "first", "second", "third" and "fourth", "primary", "secondary", "tertiary" etc. does not denote any order or importance, but rather the terms "first", "second", "third" and "fourth", "primary", "secondary", "tertiary" etc. are used to distinguish one element from another. Note that the words "first", "second", "third" and "fourth", "primary", "secondary", "tertiary" etc. are used here and elsewhere for labelling purposes only and are not intended to denote any specific spatial or temporal ordering. Furthermore, the labelling of a first element does not imply the presence of a second element and vice versa.

Although particular features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications and equivalents.

LIST OF REFERENCES 1 ostomy system
2 ostomy appliance
4 base plate
6 monitor device
8 accessory device
10 server device
12 network
14 coupling member
16 coupling ring
18, 18A, 18B, 18C, 18D stomal opening
19 center point
20 docking station
22 first connector
24 user interface
100 monitor device housing
101 processor
102 first interface
104 second interface
106 memory
108 ground terminal of monitor device
110 first terminal of monitor device
112 second terminal of monitor device
114 third terminal of monitor device
116 fourth terminal of monitor device
118 fifth terminal of monitor device
120 coupling part
121 power unit
122 antenna 124 wireless transceiver
126 loudspeaker
128 haptic feedback element
130 data collection schemes
131 primary data collection scheme
132 secondary data collection scheme
133 data collector
134 data collection unit
135 data collection controller
136A first control pin
136B second control pin
137A first primary data pin
137B second primary data pin
138A first secondary data pin
138B second secondary data pin
138 primary data collection scheme
139 analog-to-digital converter
140 sensor unit
141 multiplexer
200 first adhesive layer
200A distal surface of first adhesive layer
200B proximal surface of first adhesive layer
202 second adhesive layer
202A distal surface of second adhesive layer
202B proximal surface of second adhesive layer
204 electrode assembly
204A distal surface of electrode assembly
204B proximal surface of electrode assembly
206 release liner
206A distal surface of the release liner
206B proximal surface of the release liner
208 top layer
208A distal surface of the top layer
208B proximal surface of the top layer
209 coupling ring
210 coupling part of first connector
211 first connector
212 terminals of first connector
213 first intermediate element
213A distal surface of first intermediate element
213B proximal surface of first intermediate element
214 support layer of electrode assembly
214A distal surface of support layer
214B proximal surface of support layer
216 electrodes of electrode assembly
217 connection parts of electrodes
218, 219 masking element
218A distal surface of masking element
218B proximal surface of masking element
220, 220A, 220B electrode configuration
222 ground electrode
222A ground connection part
222B ground sensing part
224 first electrode
224A first connection part
224B first sensing part
226 second electrode
226A second connection part
226B second sensing part
228 third electrode
228A third connection part
228B third sensing part
230 fourth electrode
230A fourth connection part
230B fourth sensing part
232 fifth electrode
232A fifth connection part
232B fifth sensing part
234 first electrode part of the ground electrode
236 second electrode part of the ground electrode
238 third electrode part of the ground electrode
240 fourth electrode part of the ground electrode
242 ground terminal opening
244 first terminal opening
246 second terminal opening
248 third terminal opening
250 fourth terminal opening
252 fifth terminal opening
254 primary sensor point openings of masking element
254A primary first sensor point opening
254B primary second sensor point opening
256 secondary sensor point openings of masking element
256A secondary first sensor point opening
256B secondary second sensor point opening
258 tertiary sensor point openings of masking element
258A tertiary first sensor point opening
258B tertiary second sensor point opening
260 primary sensor point openings of first adhesive layer
260A primary first sensor point opening
260B primary second sensor point opening
262 secondary sensor point openings of first adhesive layer
262A secondary first sensor point opening
262B secondary second sensor point opening
264 tertiary sensor point openings of first adhesive layer
264A tertiary first sensor point opening
264B tertiary second sensor point opening
282 ground terminal element
282A ground terminal
284 first terminal element
284A first terminal
286 second terminal element
286A second terminal
288 third terminal element
288A third terminal
290 fourth terminal element
290A fourth terminal
292 fifth terminal element
292A fifth terminal
300 method of data collection from an ostomy appliance
302 collecting data according to a primary data collection scheme
304 collecting data according to a secondary data collection scheme
306 selecting the data collection scheme
1100 curve showing, as a function of time, a first parameter data indicative of voltage measured by the first electrode pair of the base plate
1102 curve showing, as a function of time, a second parameter data indicative of voltage measured by the second electrode pair of the base plate
1104 curve showing, as a function of time, a third parameter data indicative of voltage measured by the third electrode pair of the base plate
1108 curve showing, as a function of time, a fourth primary parameter indicative of voltage measured by the fourth electrode pair of the base plate
1110 curve showing, as a function of time, a gradient of fourth primary parameter indicative of voltage gradient
1112 curve showing, as a function of time, a gradient of fourth secondary parameter indicative of voltage gradient measured 1114 curve showing, as a function of time, a gradient of fourth tertiary parameter indicative of voltage gradient measured 1116 curve showing, as a function of time, a fourth secondary parameter indicative of voltage measured 1118 curve showing, as a function of time, a fourth tertiary parameter indicative of voltage measured 1200 curve showing, as a function of time, a third parameter data indicative of voltage measured by the third electrode pair of the base plate 1202 curve showing, as a function of time, a first parameter data indicative of voltage measured by the first electrode pair of the base plate 1204 curve showing, as a function of time, a second parameter data indicative of voltage measured by the second electrode pair of the base plate 1206 curve showing, as a function of time, a fourth primary parameter indicative of voltage measured by the fourth electrode pair of the base plate 1208 curve showing, as a function of time, a fourth secondary parameter indicative of voltage measured 1210 curve showing, as a function of time, a fourth tertiary parameter indicative of voltage measured 1212 curve showing, as a function of time, a gradient of fourth primary parameter indicative of voltage gradient measured by the fourth electrode pair of the base plate 1214 curve showing, as a function of time, a gradient of fourth secondary parameter data indicative of voltage gradient measured 1216 curve showing, as a function of time, a gradient of fourth tertiary parameter indicative of voltage gradient measured 1300 curve showing, as a function of time, a first parameter data indicative of voltage measured by the first electrode pair of the base plate 1302 curve showing, as a function of time, a second parameter data indicative of voltage measured by the second electrode pair of the base plate 1304 curve showing, as a function of time, a third parameter data indicative of voltage measured by the third electrode pair of the base plate 1306 curve showing, as a function of time, a fourth primary parameter indicative of voltage measured by the fourth electrode pair of the base plate 1308 curve showing, as a function of time, a fourth secondary parameter indicative of voltage measured 1310 curve showing, as a function of time, a fourth tertiary parameter indicative of voltage measured 1312 curve showing, as a function of time, a gradient of fourth primary parameter indicative of voltage gradient measured by the fourth electrode pair of the base plate 1314 curve showing, as a function of time, a gradient of fourth secondary parameter indicative of voltage gradient measured 1316 curve showing, as a function of time, a gradient of fourth tertiary parameter indicative of voltage gradient measured 1502 curve showing, as a function of time, a first parameter data indicative of voltage measured by the first electrode pair of the base plate 1504 curve showing, as a function of time, a second parameter data indicative of voltage measured by the second electrode pair of the base plate 1506 curve showing a diameter of the white ring as a function of time 1602 curve showing peel force applied to the first adhesive layer in a dry adhesive state as a function of peeling distance 1604 a peel force applied to the first adhesive layer as a function of a peeling distance travelled by a peeling action exercising the peel force on the first adhesive layer in a wet adhesive state 1606 a peel force applied to the first adhesive layer as a function of a peeling distance travelled by a peeling action exercising the peel force on the first adhesive layer partially wet 1608 length of the first adhesive layer 1608 in dry adhesive state 1610 the first adhesive layer which comprises a first portion in a dry adhesive state and a second portion in a wet adhesive state 1610A a first portion in a dry adhesive state 1610B a second portion in a wet adhesive state

The invention claimed is:

1. A monitor device for a medical system, the monitor device comprising:
a processor;
memory; and
a first interface connected to the processor and the memory, the first interface comprising:
a plurality of terminals including a first terminal and a second terminal, the first terminal configured to form an electrical connection with a first electrode of a medical appliance of the medical system and the second terminal configured to form an electrical connection with a second electrode of the medical appliance, and
a data collector coupled to the first terminal and the second terminal and configured to:
collect data from said first and second terminals according to a data collection scheme selected from a primary data collection scheme and a secondary data collection scheme, the primary data collection scheme being different from the secondary data collection scheme, the data collector comprising a data collection controller configured to select the data collection scheme based on a control signal indicative of the data collection scheme from the processor.

2. The monitor device of claim 1, wherein a sampling rate of the primary data collection scheme is different than a sampling rate of the secondary data collection scheme.

3. The monitor device of claim 1, wherein the processor is configured to determine the control signal based on an operating state of the medical appliance.

4. The monitor device of claim 1, wherein the processor is configured to determine the control signal in accordance with an orientation of the user.

5. The monitor device of claim 1, wherein the processor is configured to determine the control signal in accordance with an activity level of a user.

6. The monitor device of claim 1, wherein the processor is configured to determine the control signal in accordance with a distance between the controller and an accessory device.

7. The monitor device of claim 1, wherein the processor is configured to determine the control signal in accordance with a power capacity of a power unit of the monitor device.

8. The monitor device of claim 1, wherein the processor is configured to determine the control signal in accordance with a model type of the medical appliance.

9. The monitor device of claim 1, wherein the processor is configured to determine the control signal in accordance with a wear time of the medical appliance.

10. The monitor device of claim 1, wherein the processor is configured to determine the control signal in accordance with preferences of a user of the medical appliance.

11. The monitor device of claim 1, wherein the processor is configured to determine the control signal in accordance with a location of a user of the medical appliance.

12. A method for data collection from an medical appliance, the method comprising:
    selecting a data collection scheme from a primary data collection scheme and a secondary data collecting scheme, the primary data collection scheme being different from the secondary data collection scheme, in accordance with an operating state of the medical appliance,
    in accordance with selecting the primary data collection scheme; collecting data from a first terminal and a second terminal according to the primary data collection scheme, the first terminal forming an electrical connection with a first electrode of the medical appliance and the second terminal forming an electrical connection with a second electrode of the medical appliance; and
    in accordance with selecting the secondary data collection scheme; collecting data from the first terminal and the second terminal according to the secondary data collection scheme.

13. The method of claim 12, wherein a sampling rate of the primary data collection scheme is different from a sampling of the secondary data collection scheme.

14. The method of claim 1, the method comprising selecting the data collection scheme in accordance with an operating state of the medical appliance.

* * * * *